United States Patent
Ung et al.

(10) Patent No.: US 9,238,709 B2
(45) Date of Patent: Jan. 19, 2016

(54) LATENT, HIGH-ACTIVITY OLEFIN METATHESIS CATALYSTS CONTAINING AN N-HETEROCYCLIC CARBENE LIGAND

(71) Applicants: MATERIA, INC., Pasadena, CA (US); CALIFORNIA INSTITUTE OF TECHNOLOGY, Pasadena, CA (US)

(72) Inventors: Thay Ung, Los Angeles, CA (US); Yann Schrodi, Pasadena, CA (US); Mark S. Trimmer, Monrovia, CA (US); Andrew Hejl, Pasadena, CA (US); Daniel Sanders, Pasadena, CA (US); Robert H. Grubbs, South Pasadena, CA (US)

(73) Assignees: MATERIA, INC., Pasadena, CA (US); CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

(21) Appl. No.: 14/497,387

(22) Filed: Sep. 26, 2014

(65) Prior Publication Data

US 2015/0141603 A1    May 21, 2015

Related U.S. Application Data

(63) Continuation of application No. 13/779,190, filed on Feb. 27, 2013, now Pat. No. 8,871,879, which is a continuation of application No. 11/094,102, filed on Mar. 29, 2005, now abandoned.

(60) Provisional application No. 60/557,742, filed on Mar. 29, 2004, provisional application No. 60/604,158, filed on Aug. 23, 2004.

(51) Int. Cl.
*C08F 132/08*    (2006.01)
*C07C 67/333*    (2006.01)
(Continued)

(52) U.S. Cl.
CPC .............. *C08G 61/02* (2013.01); *C07C 67/333* (2013.01); *C07D 493/10* (2013.01);
(Continued)

(58) Field of Classification Search
USPC .................................. 526/171; 502/155, 167
See application file for complete search history.

(56) References Cited

U.S. PATENT DOCUMENTS

| 5,312,940 A | 5/1994 | Grubbs et al. |
| 5,969,170 A | 10/1999 | Grubbs et al. |

(Continued)

FOREIGN PATENT DOCUMENTS

| WO | 99/51344 | 10/1999 |
| WO | 00/71554 A2 | 11/2000 |

OTHER PUBLICATIONS

Blackwell, et al., "New approaches to olefin cross metathesis," J. Am. Chem. Soc. (2000) 122:58-71.

(Continued)

*Primary Examiner* — Robert Harlan
(74) *Attorney, Agent, or Firm* — J.A. Lindeman & Co., PLLC

(57) ABSTRACT

The invention provides novel organometallic complexes useful as olefin metathesis catalysts. The complexes have an N-heterocyclic carbene ligand and a chelating carbene ligand associated with a Group 8 transition metal center. The molecular structure of the complexes can be altered so as to provide a substantial latency period. The complexes are particularly useful in catalyzing ring closing metathesis of acyclic olefins and ring opening metathesis polymerization of cyclic olefins.

21 Claims, 18 Drawing Sheets

Catalyst 2a

Catalyst 2b

(51) Int. Cl.
*B01J 31/22* (2006.01)
*C08G 61/02* (2006.01)
*C07F 15/00* (2006.01)
*C08G 61/06* (2006.01)
*C07D 493/10* (2006.01)

(52) U.S. Cl.
CPC .......... *C07F 15/0046* (2013.01); *C08F 132/08* (2013.01); *C08G 61/06* (2013.01); *C08G 2261/11* (2013.01); *C08G 2261/3325* (2013.01); *C08G 2261/418* (2013.01)

(56) References Cited

U.S. PATENT DOCUMENTS

| | | | |
|---|---|---|---|
| 6,077,805 | A | 6/2000 | Van Der Schaaf et al. |
| 6,107,420 | A | 8/2000 | Grubbs et al. |
| 6,111,121 | A | 8/2000 | Grubbs et al. |
| 6,306,987 | B1 * | 10/2001 | Van Der Schaaf et al. ... 526/171 |
| 6,803,429 | B2 * | 10/2004 | Morgan et al. ............... 526/135 |
| 6,884,859 | B2 | 4/2005 | Grubbs et al. |
| 2002/0177710 | A1 | 11/2002 | Grubbs et al. |

OTHER PUBLICATIONS

Chatterjee et al. (2000), "Synthesis of functionalized Olefins by Cross and Ring-Closing Metatheses," J. Am. Chem. Soc. 122(15):3783-3784.
Chatterjee, et al., "Formyl vinyl C-H activation and allylic oxidation by olefin metathesis," Angew. Chem. Intl. Ed. (2000) 41:3171-3174.
Chatterjee, et al., "A general model for selectivity in olefin cross metathesis," J. Am. Chem. Soc. (2003) 125:111360-11370.
Choi, et al., "Controlled living ring opening metathesis polymerization by fast initiating ruthenium catalyst," Angew. Chem. Intl. Ed. (2003) 42; 1743-1746.
Conrad, et al., "The first highly active halide-free ruthenium catalyst for olefin metathesis," Organometallics (2003) 22:3634-3636.
Courchay, et al., "Metathesis activity and stability of new generation ruthenium polymerization catalysts," Macromolecules (2003) 36:8231-8239.
Dinger, et al., "High turnover numbers with ruthenium-based metathesis catalysts," Adv. Synth. Catal. (2002) 344:671-677.
Furstner, et al., "Study concerning the effects of chelation on the structure and catalytic activity of . ruthenium carbene complexes," Organometallics (2002) 21:331-335.
Furstner, et al., "Comparative investigation of ruthenium-based metathesis catalysts bearing N-heterocyclic carbene (NHC) ligands," Chem. Eur. J. (2001) 15:3236-3253.
Garber, et al., "Recyclable and efficient monomeric and dendritic Ru-based metathesis catalysts," J. Am. Chem. Soc. (2000) 122:8168-8179.
Grubbs, "Handbook of Metathesis," vols. I, 2 and 3, Wiley VCH, Weinheim, 2003.
Grubbs, et al., "Recent advances in olefin metathesis and its application in organic synthesis," Tetrahedron (1998) 54:4413-4450.
Harrity. et al., "Ru-catalyzed rearrangement of styrenyl ethers. Enantioselective synthesis of chromenes through Zr- and Ru-catalyzed processes," J. Am. Chem. Soc. (1997) 119:1488-1489.
Harrity, et al., "Chromenes through metal-catalyzed reactions of styrenyl ethers. Mechanism and utility in synthesis," J. Am. Chem. Soc. (1998) 120:2343-2351.
Kingsbury, et al., "A recyclable ruthenium-based metathesis catalyst," J. Am. Chem. Soc. (1999) 121:791-799.
Love, et al., "A practical and highly active ruthenium-based catalyst that effects cross metathesis of acrylonitrile," Angew. Chem. Intl. Ed. 41:4035-4037.
Love, et al., "Synthesis, structure and activity of enhanced initiators for olefin metathesis," J. Am. Chem. Soc. (2003) 125:10103-10109.
Nguyen, et al., "Ring-opening metathesis polymerization (ROMP) of norbornene by a group VIII carbine complex. in protic media," J. Am. Chem. Soc. (1992) 114:3974-3975.
Sanford, et al., "A versatile precursor for the synthesis of ruthenium olefin• metathesis catalysts," Organometallics (2001) 20:5314-5318.
Scholl et al. (1999), "Synthesis and Activity of a New Generation of Ruthenium-Based Olefin Metathesis Catalysts Coordinated with 1,3-Dimesityl-4,5-dihydroimidazol-2-ylidene Ligands," Organic Letters 1(6):953-956.
Schrock, "Olefin metathesis reactions catalyzed by molybdenum alkylidenes," Tetrahedron (1999) 55:8141-8153.
Schrock, "Living ring-opening metathesis polymerization catalyzed by well characterized transition metal alkylidene complexes," Acc. Chem. Res. (1990) 23:158-165.
Schwab, et al., "A series of well-defined metathesis catalysts—synthesis of[RuC12(=CHR')(PR3)2] and its reactions," Angew. Chem. Inli. Ed. Engl. (1995) 34:2039-2041.
Schwab, et al., "Synthesis and applications of RuC12 (=CNR ')(PR3)2: the influence of the alkylidene moiety on metathesis activity," J. Am. Chem. Soc. (1996) 118:100-110.
Slugovc, et al., "'Second generation' ruthenium carbene complexes with a cis-dichloro arrangement," Organometallics (2004) 23:3622-3626.
Trnka et al. (2001), "The Development of X2X2Ru=CHR Olefin Metathesis Catalysts: An Organometallic Success Story," Acc. Chem. Res. 34(1): 18-29.
Van der Schaaf, et al., "Synthesis and reactivity of novel ruthenium carbene catalysts. X-ray structures of [RuCl2(CHSC6H5)(pipr3)2] and [RuC12(CHCH 2CH2-C-N-C5H4)(Npipr3)]," J. Organometallic Chem. (2000) 606:65-74.
Dragutan, et al., "N-Heterocyclic Carbenes as Highly Efficient Ancillary Ligands in Homogeneous and Immobilized Metathesis Ruthenium Catalytic Systems," Arkivoc (2005) x:206-253.

* cited by examiner

LATENT, HIGH-ACTIVITY OLEFIN METATHESIS CATALYSTS CONTAINING AN N-HETEROCYCLIC CARBENE LIGAND

CROSS-REFERENCE TO RELATED APPLICATIONS

This application claims priority under 35 U.S.C. §119(e)(1) to U.S. patent application Ser. No. 13/779,190, filed Feb. 27, 2013; which claims priority to U.S. patent application Ser. No. 11/094,102, filed Mar. 29, 2005; which claims priority to U.S. Provisional Application No. 60/557,742, filed Mar. 29, 2004, and U.S. Provisional Application No. 60/604,158, filed Aug. 23, 2004. The disclosures of the aforementioned provisional patent applications are incorporated by reference herein.

STATEMENT OF GOVERNMENT RIGHTS

This invention was made with government support under Grant No. GM 068647 awarded by the National Institutes of Health and Grant No. CHE-0111946 awarded by the National Science Foundation. The government has certain rights in the invention.

TECHNICAL FIELD

This invention relates generally to olefin metathesis catalysts, and more particularly pertains to new Group 8 transition metal complexes that are useful as latent olefin metathesis catalysts. The invention has utility in the fields of catalysis, organic synthesis, and organometallic chemistry.

BACKGROUND OF THE INVENTION

Olefin metathesis catalysis is a powerful technology, which in recent years has received tremendous attention as a versatile method for the formation of carbon-carbon bonds and has numerous applications in organic synthesis and polymer chemistry (R. H. Grubbs, *Handbook of Metathesis*, Vol. 2 and 3; Wiley VCH, Weinheim, 2003). The family of olefin metathesis reactions includes ring-closing metathesis (RCM), cross metathesis (CM), ring-opening metathesis polymerization (ROMP), and acyclic diene metathesis polymerization (ADMET). The success of olefin metathesis stems from the development of several well-defined transition metal complexes, such as the Schrock molybdenum catalysts and the Grubbs ruthenium and osmium catalysts (see, e.g., Schrock (1999) *Tetrahedron* 55, 8141-8153; Schrock (1990) *Acc. Chem. Res.* 23, 158-165; Grubbs et al. (1998) *Tetrahedron* 54, 4413-4450; Trnka et al. (2001) *Acc. Chem. Res.* 34, 18-29; Grubbs, *Handbook of Metathesis*, Vol. 1; Wiley VCH, Weinheim, 2003). Following the discovery of these complexes, a significant amount of olefin metathesis research has focused on tuning the ruthenium and osmium carbene catalysts in order to increase their activity, selectivity, and/or stability. The most common strategy has involved the replacement of mono-dentate ligands with other mono-dentate ligands to provide the catalytic complexes with new and useful properties.

The original breakthrough ruthenium catalysts were primarily bisphosphine complexes of the general formula $(PR_3)_2(X)_2M=CHR'$ wherein M is ruthenium (Ru) or osmium (Os), X represents a halogen (e.g., Cl, Br, or I), R represents an alkyl, cycloalkyl, or aryl group (e.g., butyl, cyclohexyl, or phenyl), and R' represents an alkyl, alkenyl, or aryl group (e.g., methyl, $CH=C(CH_3)_2$, phenyl, etc.) (see Nguyen et al. (1992) *J. Am. Chem. Soc.* 1992, 114, 3974-3975; Schwab et al. (1995) *Angew. Chem., Int. Ed.* 34, 2039-2041; Schwab et al. (1996) *J. Am. Chem. Soc.* 118, 100-110). Examples of these types of catalysts are described in U.S. Pat. Nos. 5,312,940, 5,969,170 and 6,111,121 to Grubbs et al. While such complexes are capable of catalyzing a considerable number of olefin metathesis transformations, these bisphosphine complexes can exhibit lower activity than desired and, under certain conditions, can have limited lifetimes.

More recent developments in the field have led to greatly increased activity and stability by replacing one of the phosphine ligands with a bulky N-heterocyclic carbene (NHC) ligand (Scholl et al. (1999) *Organic Letters* 1, 953-956) to give complexes of the general formula $(L)(PR_3)(X)_2Ru=CHR'$, wherein L represents an NHC ligand such as 1,3-dimesitylimidazole-2-ylidene (IMes) and 1,3-dimesityl-4,5-dihydroimidazol-2-ylidene (sIMes), X represents a halogen (e.g., Cl, Br, or I), R represents an alkyl, cycloalkyl, or aryl group (e.g., butyl, cyclohexyl, or phenyl), and R' represents an alkyl, alkenyl, or aryl group (e.g., methyl, $CH=C(CH_3)_2$, phenyl, etc.). Representative structures include complex A (ibid.), complex B (Garber et al. (2000) *J. Am. Chem. Soc.* 122, 8168-8179), and complex C (Sanford et al. (2001) *Organometallics* 20, 5314-5318; Love et al. (2002) *Angew. Chem., Int. Ed.* 41, 4035-4037):

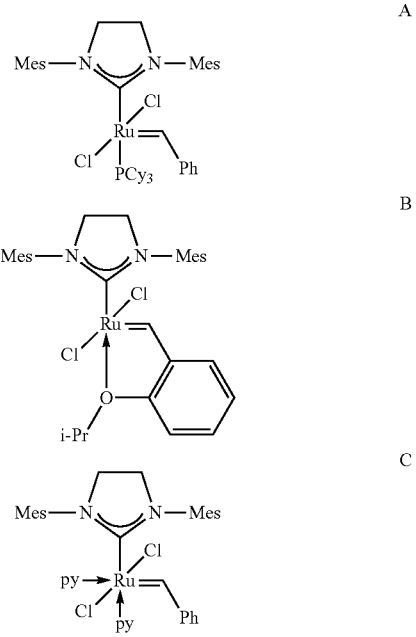

Unlike prior bisphosphine complexes, the various imidazolylidine catalysts effect the efficient formation of trisubstituted and tetrasubstituted olefins through catalytic metathesis. Examples of these types of catalysts are described in PCT publications WO 99/51344 and WO 00/71554. Further examples of the synthesis and reactivity of some of these active ruthenium complexes are reported by Fürstner et al. (2001) *Chem. Eur. J.* 7, No. 15, 3236-3253; Blackwell et al. (2000) *J. Am. Chem. Soc.* 122, 58-71; Chatterjee et al. (2000) *J. Am. Chem. Soc.* 122, 3783-3784; Chatterjee et al. (2000) *Angew. Chem. Int. Ed.* 41, 3171-3174; Chatterjee et al. (2003) *J. Am. Chem. Soc.* 125, 11360-11370. Further tuning of these catalysts led to even higher activity by using bulkier imidazolylidine ligands such as 1,3-bis(2,6-diisopropylphenyl)-4, 5-dihydroimidazol-2-ylidenes (Dinger et al. (2002) *Adv. Synth. Catal.* 344, 671-677) or electron deficient phosphine ligands such as fluorinated aryl phosphines (Love et al. (2003) *J. Am. Chem. Soc.* 125, 10103-10109).

Another example of ligand substitution that has led to enhanced catalyst activity is the replacement of the phosphine ligand in the (L)(PR$_3$)(X)$_2$M=CHR' complexes with one or two pyridine-type ligands to give compounds of the general formula (L)(L')$_n$(X)$_2$M=CHR' wherein n=1 or 2, L represents an imidazolylidine ligand, L' represents a pyridine (Py) or substituted pyridine ligand, X represents a halogen (e.g., Cl, Br, or I), and R' represents an alkyl, alkenyl, or aryl group (e.g., methyl, CH=C(CH$_3$)$_2$, phenyl, etc.). These pyridine complexes are extremely fast-initiating and catalyze living ring-opening metathesis polymerizations (Choi et al. (2003) *Chem. Int. Ed.* 42, 1743-1746) as well as highly challenging processes such as olefin cross metathesis with acrylonitrile (Love et al. (2002) *Angew. Chem. Int. Ed.* 41, 4035-4037).

Yet another example of mono-dentate ligand substitution is the replacement of the halogen ligands with aryl-oxo ligands, which in one example has led to a catalyst with enhanced activity: (L)(L')$_n$(RO)$_2$Ru=CHR' wherein n=1, L represents an imidazolylidine ligand, L' represents a pyridine ligand, R represents a fluorinated aryl group, and R' represents an alkyl, alkenyl, or aryl group (Conrad et al. (2003) *Organometallics* 22, 3634-3636).

A different strategy to tune olefin metathesis catalysts involves linking two of the ligands that are attached to the metal center. Of particular interest are the chelating carbene species reported by Hoveyda and others (Gaber et al. (2000) *J. Am. Chem. Soc.* 122, 8168-8179; Kingsbury et al. (1999) *J. Am. Chem. Soc.* 121, 791-799; Harrity et al. (1997) *J. Am. Chem. Soc.* 119, 1488-1489; Harrity et al. (1998) *J. Am. Chem. Soc.* 120, 2343-2351). These catalysts are exceptionally stable and can be purified by column chromatography in air. Representative such catalysts, designated Catalyst PR-1 and PR-2, are illustrated in FIG. 1. Catalyst PR-2 combines excellent stability and enhanced activity, and actively promotes the cross-metathesis of acrylonitrile and terminal olefins in moderate to excellent yields.

While most of these efforts have focused on increasing the activity and initiation rate of the ruthenium carbene metathesis catalysts, there remains a need for highly active catalysts that initiate more slowly (i.e., are more latent). This can be a particularly beneficial feature when performing metathesis polymerizations, which, in practice, typically require a significant period of time (the "work-time") within which to mix, handle, and process the catalyst/resin mixture before it gels or solidifies. For one-part catalyst systems, such as the metal carbene olefin metathesis catalysts, latency is generally achieved through temperature variation. Either the catalyst/resin mixture can be handled at a low enough temperature to sufficiently inhibit polymerization or the catalyst must be designed to be heat-activated to allow sufficient work-time at ambient temperatures.

One example of a thermally activated, latent metathesis polymerization catalyst system utilizing slower initiating ruthenium and osmium vinylidene complexes was described in U.S. Pat. No. 6,107,420. However, only a modest degree of control of the latency can be achieved by varying the identity of the substituent groups of the vinylidene ligand and such vinylidene complexes are often not efficient metathesis catalysts for unstrained olefins. Another example of a latent olefin metathesis catalyst that contains a chelating carbene ligand is the 2-pyridylethanyl ruthenium carbene complex (PR$_3$)(Cl)$_2$Ru(CH(CH$_2$)$_2$—C,N-2-C$_5$H$_4$N) by reacting a (PR$_3$)$_2$(Cl)$_2$Ru=CHR' complex with 2-(3-butenyl)pyridine developed by van der Schaaf (van der Schaaf et al. (2000) *J. Organometallic Chemistry* 606, 65-74). These types of catalysts are also described in U.S. Pat. No. 6,306,987. Although these catalysts do initiate more slowly than their bis-phosphine counterparts, they lack the high activity of the NHC catalyst systems. A further type of latent olefin metathesis catalysts is described by van der Schaaf in U.S. Pat. No. 6,077,805. These latter catalysts are hexacoordinate ruthenium or osmium complexes wherein two of the six ligands are preferably pyridine ligands.

In trying to develop new examples of latent, high-activity catalysts containing NHC ligands, the teaching in the prior art provides no clear direction. U.S. Pat. No. 6,077,805 teaches that hexacoordinate phosphine-ligated complexes of the general structure (PR$_3$)(X)$_2$(L)$_2$M=CHR', wherein the L ligands are pyridines or substituted pyridines or together are chelating bipyridines, are latent metathesis catalysts. Data presented in U.S. Patent Application Publication Number 2002/0177710 confirm the latency of such catalysts but also show that, in contrast, related hexacoordinate NHC-ligated complexes of the general structure (NHC)(X)$_2$(L)$_2$M=CHR' are not latent catalysts but, in fact, are actually some of the most rapidly initiating catalysts of this type ever observed (e.g., cf. Choi et al. (2003) *Angew. Chem. Int. Ed.* 42, 1743-1746 and Love et al. (2002 *Angew. Chem. Int. Ed.* 41, 4035-4037). U.S. Pat. No. 6,306,987 teaches that phosphine-ligated bridging carbene complexes of the general structure D are latent metathesis catalysts, whereas similar NHC-ligated complexes of the general structure E are not (e.g., Courchay et al. (2003) *Macromolecules* 36, 8231-8239). These observations suggest that it is difficult to achieve latency with the high-activity catalysts comprising NHC ligands.

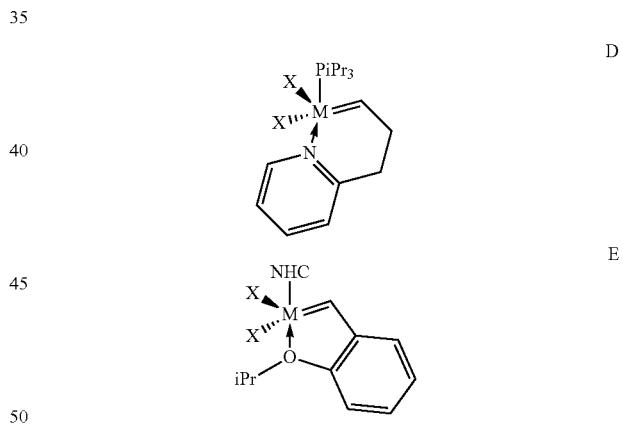

Accordingly, despite advances in the art, there is a continuing need for olefin metathesis catalysts that initiate slowly while maintaining the high activity associated with NHC-based catalysts.

SUMMARY OF THE INVENTION

The present invention relates to novel high-activity but latent olefin metathesis catalysts that comprise an NHC ligand and a chelating carbene ligand. By careful choice of the chelating carbene ligand, catalysts are provided that have a latency period on the order of minutes to hours, or even longer. It has also been surprisingly discovered that the initiation rate of some of these catalysts can be substantially varied via simple isomerization of the complexes and that the reactivity can be tuned over a wide range by controlling the ratio of the different isomers. The catalysts are particularly useful in the RCM of acyclic olefins and the ROMP of cyclic olefins.

The present catalytic complexes generally have the structure of formula (I)

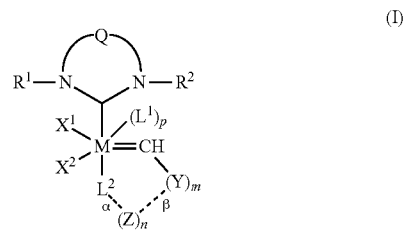

(I)

wherein:

the bonds indicated as dashed lines and designated as α and β represent single bonds or unsaturated (e.g., double) bonds, with the proviso that α and β cannot both be unsaturated bonds;

M is a Group 8 transition metal, generally ruthenium (Ru) or osmium (Os);

$R^1$ and $R^2$ are independently selected from hydrogen, hydrocarbyl, substituted hydrocarbyl, heteroatom-containing hydrocarbyl, substituted heteroatom-containing hydrocarbyl, and functional groups;

Q is an organic diradical, i.e., a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form an additional cyclic group;

$X^1$ and $X^2$ are anionic ligands, and may be the same or different;

$L^1$ is a neutral electron donor ligand, and p is zero or 1;

when α is a single bond, $L^2$ is selected from $NR^7R^8$, $PR^7R^8$, $N=CR^7R^8$, and $R^7C=NR^8$, where $R^7$ and $R^8$ are independently selected from substituted and/or heteroatom-containing $C_1$-$C_{20}$ alkyl, $C_2$-$C_{20}$ alkenyl, $C_2$-$C_{20}$ alkynyl, and $C_5$-$C_{24}$ aryl, or $R^7$ and $R^8$ can be taken together to form a heterocyclic ring;

when α is an unsaturated bond, e.g., a double bond, $L^2$ is selected from $NR^7$ and $PR^7$, where $R^7$ is as defined previously;

Y and Z are linkages independently selected from hydrocarbylene, substituted hydrocarbylene, heteroatom-containing hydrocarbylene, substituted heteroatom-containing hydrocarbylene, —O—, —S—, —$NR^9$—, and —$PR^9$—, wherein $R^9$ is selected from hydrocarbyl, substituted hydrocarbyl, heteroatom-containing hydrocarbyl, and substituted heteroatom-containing hydrocarbyl, and further wherein Y and Z, or $L^2$ and Z, may represent adjacent atoms in an aromatic ring;

m is zero or 1; and n is zero or 1, and also include isomers thereof.

In another embodiment, a method for carrying out an olefin metathesis reaction is provided using the aforementioned complexes as reaction catalysts.

BRIEF DESCRIPTION OF THE DRAWINGS

FIG. 3 depicts an ORTEP drawing of the X-ray crystal structure of Catalyst 2a.

DETAILED DESCRIPTION OF THE INVENTION

Figure 1:
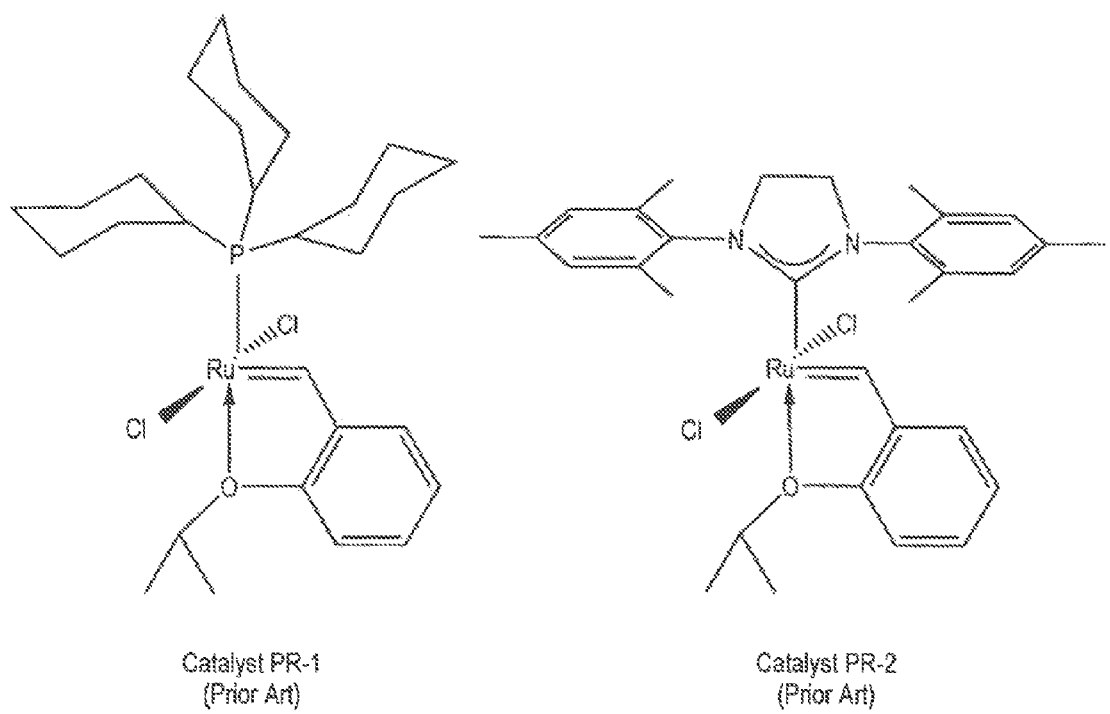
FIG. 1 provides the molecular structures of two metathesis catalysts of the prior art, indicated as Pr-1 and Pr-2.

It is to be understood that unless otherwise indicated this invention is not limited to specific reactants, reaction conditions, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a catalyst" or "a complex" encompasses a combination or mixture of different catalysts or complexes as will as a single catalyst or complex, reference to "a substituent" includes a single substituent as well as two or more substituents that may or may not be the same, and the like.

In this specification and in the claims that follow, reference will be made to a number of terms, which shall be defined to have the following meanings.

The phrase "having the formula" or "having the structure" is not intended to be limiting and is used in the same way that the term "comprising" is commonly used.

The term "alkyl" as used herein refers to a linear, branched, or cyclic saturated hydrocarbon group typically although not necessarily containing 1 to about 20 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 20 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkynylene" as used herein refers to a difunctional alkynyl group, where "alkynyl" is as defined above.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl," as used herein and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The term "cyclic" refers to alicyclic or aromatic substituents that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, and fluoro or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{20}$ alkoxy, $C_2$-$C_{20}$ alkenyloxy, $C_2$-$C_{20}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{20}$ alkylcarbonyl (—CO— alkyl) and $C_6$-$C_{24}$ arylcarbonyl (—CO-aryl)), acyloxy (—O-acyl, including $C_2$-$C_{20}$ alkylcarbonyloxy (—O—CO-alkyl) and $C_6$-$C_{24}$ arylcarbonyloxy (—O—CO-aryl)), $C_2$-$C_{20}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{20}$ alkylcarbonato (—O—(CO)—O-alkyl), $C_6$-$C_{24}$ arylcarbonato (—O—(CO)—O-aryl), carboxy (—COOH), carboxylato (—COO⁻), carbamoyl (—(CO)—NH$_2$), mono-($C_1$-$C_{20}$ alkyl)-substituted carbamoyl (—(CO)—NH($C_1$-$C_{20}$ alkyl)), di-($C_1$-$C_{20}$ alkyl)-substituted carbamoyl (—(CO)—N($C_1$-$C_{20}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{20}$ alkyl),N—($C_5$-$C_{24}$ aryl)-substituted carbamoyl, thiocarbamoyl (—(CS)—NH$_2$), mono-($C_1$-$C_{20}$ alkyl)-substituted thiocarbamoyl (—(CO)—NH($C_1$-$C_{20}$ alkyl)), di-($C_1$-$C_{20}$ alkyl)-substituted thiocarbamoyl (—(CO)—N($C_1$-$C_{20}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{20}$ alkyl),N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), isocyano (—N+≡C⁻), formyl (—(CO)—H), thioformyl (—(CS)—H), amino (—NH$_2$), mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, $C_2$-$C_{20}$ alkylamido (—NH—(CO)-alkyl), $C_6$-$C_{24}$ arylamido (—NH—(CO)-aryl), imino (—CR=NH where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O⁻), $C_1$-$C_{20}$ alkylsulfanyl (—S-alkyl; also termed "alkylthio"), $C_5$-$C_{24}$ arylsulfanyl (—S-aryl; also termed "arylthio"), $C_1$-$C_{20}$ alkyldithio (—S—S-alkyl), $C_5$-$C_{24}$ aryldithio (—S—S-aryl), $C_1$-$C_{20}$ alkylsulfinyl (—(SO)-alkyl), $C_5$-$C_{24}$ arylsulfinyl (—(SO)-aryl), $C_1$-$C_{20}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (—P(O)(O⁻), phospho (—PO$_2$), phosphino (—PH$_2$), silyl (—SiR$_3$ wherein R is hydrogen or hydrocarbyl), and silyloxy (—O-silyl), and the hydrocarbyl moieties $C_1$-$C_{20}$ alkyl (preferably $C_1$-$C_{12}$ alkyl, more preferably $C_1$-$C_6$ alkyl), $C_2$-$C_{20}$ alkenyl (preferably $C_2$-$C_{12}$ alkenyl, more preferably $C_2$-$C_6$ alkenyl), $C_2$-$C_{20}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

In the molecular structures herein, the use of bold and dashed lines to denote particular conformation of groups follows the IUPAC convention. A bond indicated by a broken line indicates that the group in question is below the general plane of the molecule as drawn, and a bond indicated by a bold line indicates that the group at the position in question is above the general plane of the molecule as drawn.

In one embodiment, then, the invention provides a Group 8 transition metal complex having the structure of formula (I)

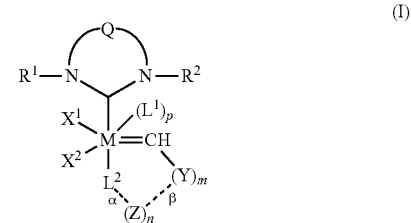

(I)

wherein:
the bonds indicated as dashed lines and designated as α and β represent single bonds or unsaturated (e.g., double) bonds, with the proviso that α and β cannot both be unsaturated bonds;

M is a Group 8 transition metal;

$R^1$ and $R^2$ are independently selected from hydrogen, hydrocarbyl, substituted hydrocarbyl, heteroatom-containing hydrocarbyl, substituted heteroatom-containing hydrocarbyl, and functional groups;

Q is an organic diradical, i.e., a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form an additional cyclic group;

$X^1$ and $X^2$ are anionic ligands, and may be the same or different;

$L^1$ is a neutral electron donor ligand, and p is zero or 1;

when $\alpha$ is a single bond, $L^2$ is selected from $NR^7R^8$, $PR^7R^8$, $N=CR^7R^8$, and $R^7C=NR^8$, where $R^7$ and $R^8$ are independently selected from substituted and/or heteroatom-containing $C_1$-$C_{20}$ alkyl, $C_2$-$C_{20}$ alkenyl, $C_2$-$C_{20}$ alkynyl, and $C_5$-$C_{24}$ aryl, or $R^7$ and $R^8$ can be taken together to form a heterocyclic ring;

when $\alpha$ is an unsaturated bond, e.g., a double bond, $L^2$ is selected from $NR^7$ and $PR^7$, where $R^7$ is as defined previously;

Y and Z are linkages independently selected from hydrocarbylene, substituted hydrocarbylene, heteroatom-containing hydrocarbylene, substituted heteroatom-containing hydrocarbylene, —O—, —S—, —$NR^9$—, and —$PR^9$—, wherein $R^9$ is selected from hydrocarbyl, substituted hydrocarbyl, heteroatom-containing hydrocarbyl, and substituted heteroatom-containing hydrocarbyl, and further wherein Y and Z, or $L^2$ and Z, may represent adjacent atoms in an aromatic ring;

m is zero or 1; and n is zero or 1, as well as isomers thereof.

More particularly:

The metal center designated as M is a Group 8 transition metal, preferably ruthenium or osmium. In a particularly preferred embodiment, M is ruthenium.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. When $R^1$ and $R^2$ are aromatic, they are typically although not necessarily composed of one or two aromatic rings, which may or may not be substituted, e.g., $R^1$ and $R^2$ may be phenyl, substituted phenyl, biphenyl, substituted biphenyl, or the like. In one preferred embodiment, $R^1$ and $R^2$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, and halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. More preferably, $R^1$ and $R^2$ are mesityl.

In another preferred embodiment, $R^1$ and $R^2$ are independently selected from hydrogen, $C_1$-$C_{20}$ alkyl, $C_2$-$C_{20}$ alkenyl, $C_2$-$C_{20}$ alkynyl, $C_5$-$C_{24}$ substituted aryl, $C_1$-$C_{20}$ functionalized alkyl, $C_2$-$C_{20}$ functionalized alkenyl, $C_2$-$C_{20}$ functionalized alkynyl, or $C_5$-$C_{24}$ functionalized substituted aryl where the functional group(s) ("Fn") may independently be one or more of the following:

$C_1$-$C_{20}$ alkoxy, $C_5$-$C_{24}$ aryloxy, halo, carboxy (—COOH), acyl (including $C_2$-$C_{20}$ alkylcarbonyl (—CO-alkyl) and $C_6$-$C_{24}$ arylcarbonyl (—CO-aryl)), formyl (—(CO)—H), nitro (—$NO_2$), cyano(—C≡N), isocyano (—$N^+$≡$C^-$), hydroxyl, acyloxy (—O-acyl, including $C_2$-$C_{20}$ alkylcarbonyloxy (—O—CO-alkyl) and $C_6$-$C_{24}$ arylcarbonyloxy (—O—CO-aryl)), $C_2$-$C_{20}$ alkoxycarbonyl (—(CO)—O-alkyl), $C_6$-$C_{24}$ aryloxycarbonyl (—(CO)—O-aryl), $C_1$-$C_{20}$ alkoxy-substituted $C_1$-$C_{20}$ alkyl, $C_1$-$C_{20}$ alkoxy-substituted $C_5$-$C_{24}$ aryl, $C_5$-$C_{24}$ aryloxy-substituted $C_1$-$C_{20}$ alkyl, $C_5$-$C_{24}$ aryloxy-substituted $C_5$-$C_{24}$ aryl, amino (—$NH_2$), imino (—CR=NH where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), $C_2$-$C_{20}$ alkylamido (—NH—(CO)-alkyl), $C_6$-$C_{24}$ arylamido (—NH—(CO)-aryl), $C_1$-$C_{20}$ alkylsulfanyl (—S-alkyl; also termed "alkylthio"), $C_5$-$C_{24}$ arylsulfanyl (—S-aryl; also termed "arylthio"), $C_1$-$C_{20}$ alkyldithio (—S—S-alkyl), $C_5$-$C_{24}$ aryldithio (—S—S-aryl), carbamoyl (—(CO)—$NH_2$); $C_2$-$C_{20}$ alkylcarbamoyl, (—(CO)—NH-alkyl), $C_6$-$C_{20}$ arylcarbamoyl (—(CO)—NH-aryl), silyl (—$SiR_3$ wherein R is hydrogen or hydrocarbyl), silyloxy (—O-silyl), phosphino (—$PH_2$), phosphonato (—$P(O)(O^-)_2$), boryl (—$BH_2$), borono (—$B(OH)_2$), or boronato (—$B(OR)_2$ where R is alkyl or other hydrocarbyl).

Q is typically selected from hydrocarbylene (e.g., $C_1$-$C_{20}$ alkylene, $C_2$-$C_{20}$ alkenylene, $C_2$-$C_{20}$ alkynylene, $C_5$-$C_{24}$ arylene, $C_6$-$C_{24}$ alkarylene, or $C_6$-$C_{24}$ aralkylene), substituted hydrocarbylene (e.g., substituted $C_1$-$C_{20}$ alkylene, $C_2$-$C_{20}$ alkenylene, $C_2$-$C_{20}$ alkynylene, $C_5$-$C_{24}$ arylene, $C_6$-$C_{24}$ alkarylene, or $C_6$-$C_{24}$ aralkylene), heteroatom-containing hydrocarbylene (e.g., $C_1$-$C_{20}$ heteroalkylene, $C_2$-$C_{20}$ heteroalkenylene, $C_2$-$C_{20}$ heteroalkynylene, $C_5$-$C_{24}$ heteroarylene, heteroatom-containing $C_6$-$C_{24}$ aralkylene, or heteroatom-containing $C_6$-$C_{24}$ alkarylene), and substituted heteroatom-containing hydrocarbylene (e.g., substituted $C_1$-$C_{20}$ heteroalkylene, substituted $C_2$-$C_{20}$ heteroalkenylene, substituted $C_2$-$C_{20}$ heteroalkynylene, substituted $C_5$-$C_{24}$ heteroarylene, substituted heteroatom-containing $C_6$-$C_{24}$ aralkylene, or substituted heteroatom-containing $C_6$-$C_{24}$ alkarylene), wherein, as noted elsewhere herein, two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

In a more preferred embodiment, Q is a two-atom linkage having the structure —$CR^3R^4$—$CR^5R^6$— or —$CR^3$=$CR^5$—, preferably —$R^3R^4$—$CR^5R^6$—, wherein $R^3$, $R^4$, $R^5$, and $R^6$ are independently selected from hydrogen, hydrocarbyl, substituted hydrocarbyl, heteroatom-containing hydrocarbyl, substituted heteroatom-containing hydrocarbyl, and functional groups. Examples of functional groups here include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^3$, $R^4$, $R^5$, and $R^6$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^3$, $R^4$, $R^5$, and $R^6$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, $C_5$-$C_{24}$ arylsulfinyl, carboxyl, carboxylate, or triflate. Optionally, $X^1$ and $X^2$ may be substituted with one or more moieties, if the $X^1$ and/or $X^2$ substituent permits, wherein the substituents are typically although not necessarily selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$L^1$ is a neutral electron donor ligand which is coordinated to the metal center. $L^1$ may be heterocyclic, in which case it is generally selected from:

nitrogen-containing heterocycles such as pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole;

oxygen-containing heterocycles such as 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran; and mixed heterocycles such as isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

$L^1$ may also be an amine, an imine, a phosphine, an ether, or a thioether.

Preferably, $L^1$ is selected from pyridines, amines, phosphines, imines, ethers, thioethers, furans, and pyrans.

When α is a single bond, $L^2$ is selected from $NR^7R^8$, $PR^7R^8$, $N=CR^7R^8$, and $R^7C=NR^8$, where $R^7$ and $R^8$ are independently selected from substituted and/or heteroatom-containing $C_1$-$C_{20}$ alkyl, $C_2$-$C_{20}$ alkenyl, $C_2$-$C_{20}$ alkynyl, $C_5$-$C_{24}$ aryl, or $R^7$ and $R^8$ taken together can form a cyclic group, e.g., piperidyl (including substituted piperidyl). Any functional groups present on $L^1$, $L^2$, $R^7$, or $R^8$ will generally be selected from the Fn groups set forth above. Examples of preferred such catalysts are those wherein $L^2$ is $NR^7R^8$, having the structure of formula (II)

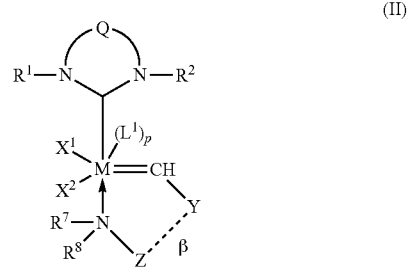

(II)

wherein Q, $R^1$, $R^2$, $R^7$, $R^8$, $X^1$, $X^2$, $L^1$, Y, Z, β, and p are as defined above. Preferred $R^7$ and $R^8$ substituents in this embodiment are $C_1$-$C_{12}$ alkyl or $C_5$-$C_{12}$ aryl, e.g., methyl, isopropyl, t-butyl, cyclohexyl, and phenyl, and preferred Y groups are —$CH_2$—, —$CH_2CH_2$— and substituted analogs thereof. Other preferred catalysts, wherein $L^2$ is $PR^7R^8$, have the structure of formula (III)

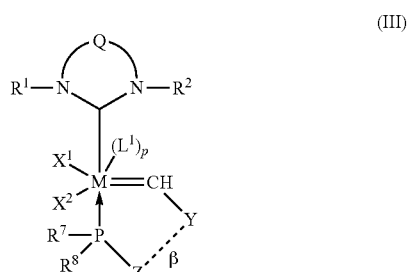

(III)

wherein Q, $R^1$, $R^2$, $R^7$, $R^8$, $X^1$, $X^2$, Y, Z, $L^1$, β, and p are as defined above, preferred $R^7$ and $R^8$ substituents are $C_1$-$C_{12}$ alkyl or $C_5$-$C_{12}$ aryl, e.g., phenyl, and preferred Y groups are as set forth for complexes of formula (II). Particularly preferred catalytic complexes encompassed by formulae (II) and (III) include, but are not limited to, the following:

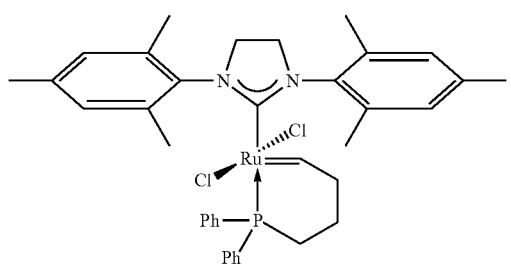

(compound 6; see Example 6)

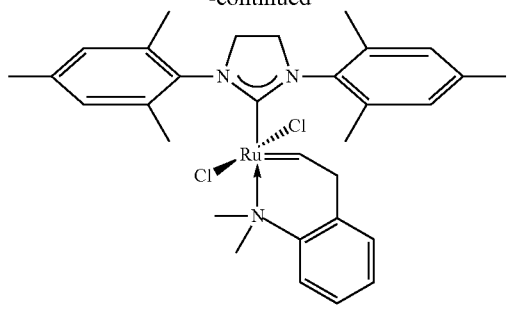

(compound 12; see Example 14)

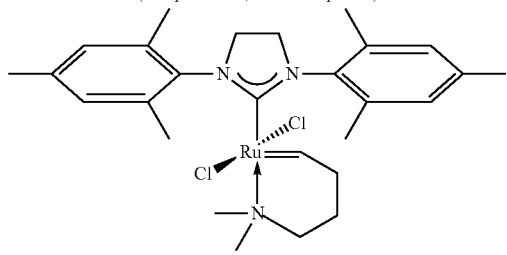

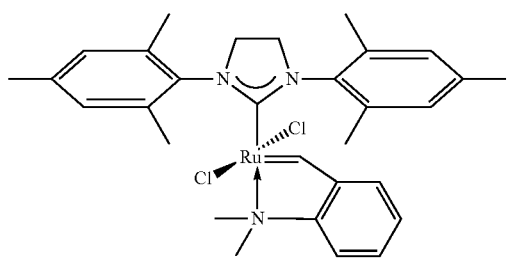

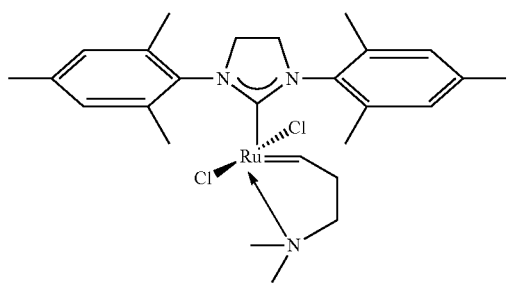

L² and Z can be linked through an unsaturated bond, i.e., the dashed line indicating a bond at α may also represent a double bond or a bond linking adjacent atoms in an aromatic ring. When L² and Z are linked through an unsaturated bond, L² is selected from NR⁷ and PR⁷, and preferably is NR⁷ where R⁷ is as defined previously. It will be appreciated that when α represents an unsaturated bond, the complex may be contain an imine ligand (i.e., containing the moiety —Z=NR⁷), or may contain a pyridine ring in which N and Z are adjacent atoms in a pyridyl group. Examples of preferred such catalysts in which the complex contains a pyridine ring or an imine moiety are encompassed by structural formulae (IV) and (V), respectively:

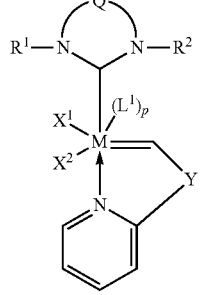

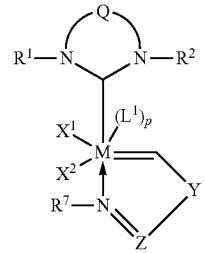

In formulae (IV) and (V), Q, $R^1$, $R^2$, $R^7$, $R^8$, $X^1$, $X^2$, Y, Z, $L^1$, β, and p are as defined above, preferred $R^7$ substituents are $C_1$-$C_{12}$ alkyl or $C_5$-$C_{12}$ aryl, e.g., methyl, isopropyl, t-butyl, cyclohexyl, and phenyl, and preferred Y groups are substituted or unsubstituted methylene or ethylene linkages.

Particularly preferred catalytic complexes encompassed by formulae (IV) and (V) include, but are not limited to, the following:

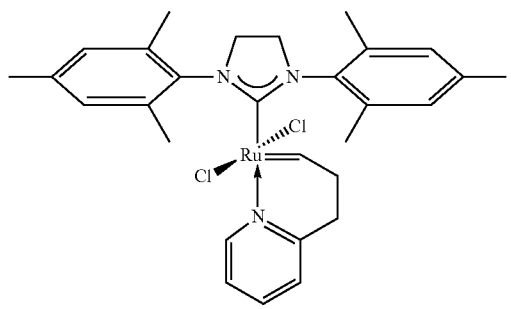

(Compound 2a; see Examples 1 and 2)

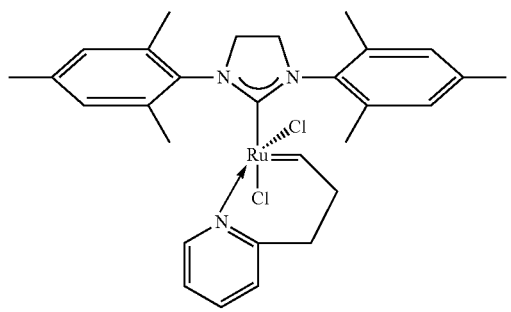

(Compound 2b; see Example 7)

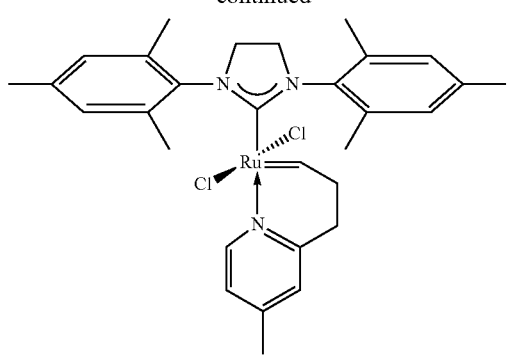

(Compound 4; see Example 5)

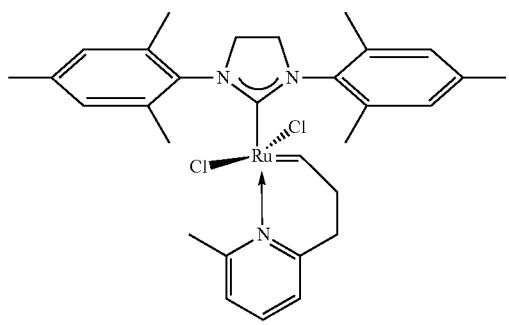

(Compound 5; see Example 5)

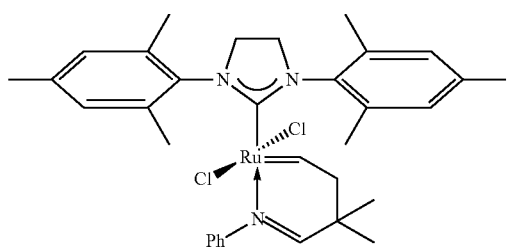

(Compound 7; see Example 9)

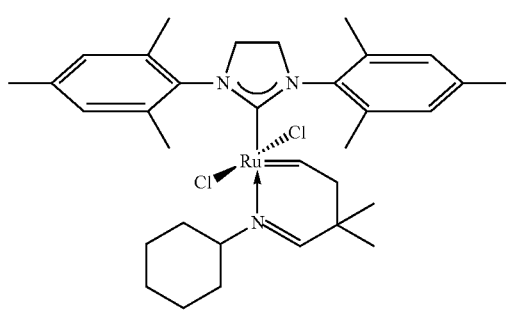

(Compound 8; see Example 10)

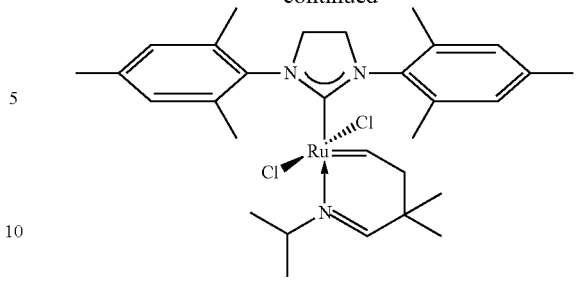

(Compound 9; see Example 11)

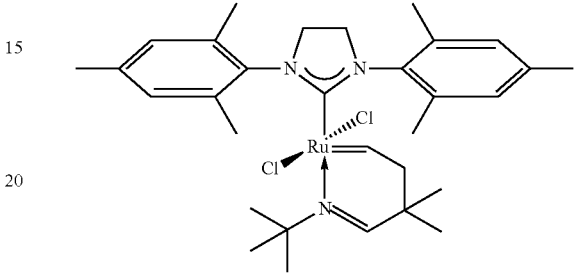

(Compound 10; see Example 12)

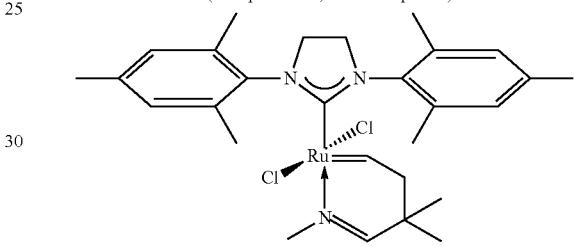

(Compound 11; see Example 13)

Y and Z are linkages independently selected from hydrocarbylene (e.g., $C_1$-$C_{20}$ alkylene, $C_2$-$C_{20}$ alkenylene, $C_2$-$C_{20}$ alkynylene, $C_5$-$C_{24}$ arylene, $C_6$-$C_{24}$ alkarylene, or $C_6$-$C_{24}$ aralkylene), substituted hydrocarbylene (e.g., substituted $C_1$-$C_{20}$ alkylene, $C_2$-$C_{20}$ alkenylene, $C_2$-$C_{20}$ alkynylene, $C_5$-$C_{24}$ arylene, $C_6$-$C_{24}$ alkarylene, or $C_6$-$C_{24}$ aralkylene), heteroatom-containing hydrocarbylene (e.g., $C_1$-$C_{20}$ heteroalkylene, $C_2$-$C_{20}$ heteroalkenylene, $C_2$-$C_{20}$ heteroalkynylene, $C_5$-$C_{24}$ heteroarylene, heteroatom-containing $C_6$-$C_{24}$ aralkylene, or heteroatom-containing $C_6$-$C_{24}$ alkarylene), substituted heteroatom-containing hydrocarbylene (e.g., substituted $C_1$-$C_{20}$ heteroalkylene, substituted $C_2$-$C_{20}$ heteroalkenylene, substituted $C_2$-$C_{20}$ heteroalkynylene, substituted $C_5$-$C_{24}$ heteroarylene, substituted heteroatom-containing $C_6$-$C_{24}$ aralkylene, or substituted heteroatom-containing $C_6$-$C_{24}$ alkarylene), —O—, —S—, —$NR^9$—, and —$PR^9$—, wherein $R^3$ is selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.). Any functional groups present on Z, Y, and/or $R^9$ will generally be selected from the Fn moieties above.

Organic diradicals that can serve as Y and/or Z include, by way of example, the following groups: methylene (VI), ethylene (VII), vinylene (VIII), phenylene (IX), cyclohexylene (X), and naphthylenes (XI) and (XII).

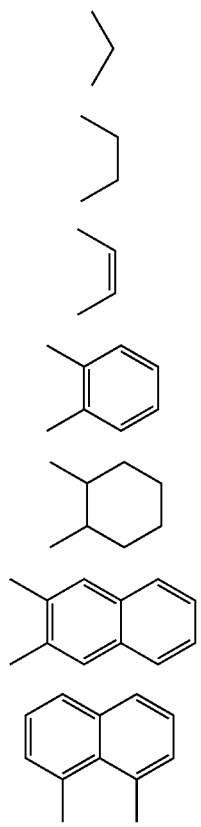

(VI)
(VII)
(VIII)
(IX)
(X)
(XI)
(XII)

These organic diradicals may also serve as the linkage Q.

In one particularly preferred embodiment of the invention, M is ruthenium, Q is ethylene (II), $X^1$ and $X^2$ are chloride, and p is zero. In a more preferred embodiment, $R^1$ and $R^2$ are mesityl(2,4,6-trimethylphenyl). In an even more preferred embodiment, n is zero.

Figure 2:
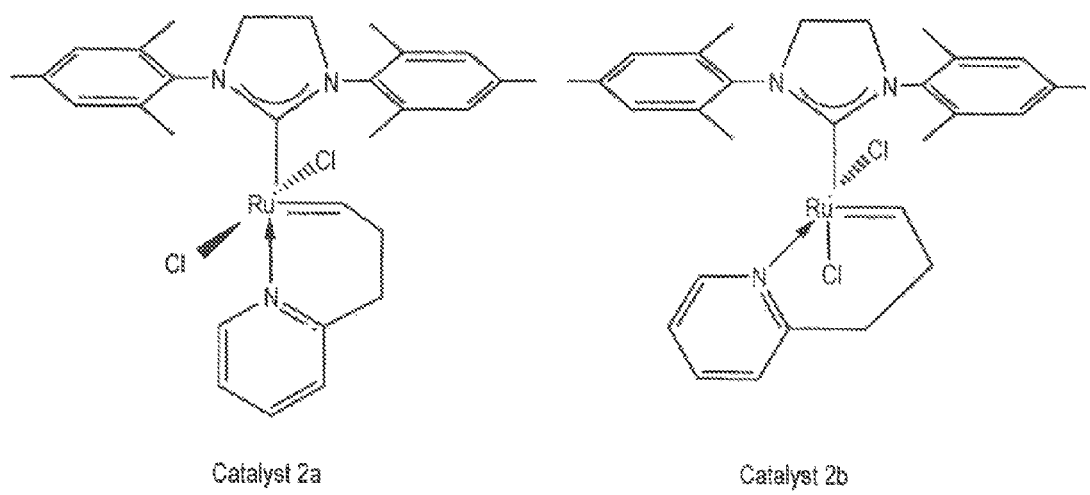
FIG. 2 provides the molecular structures of two representative catalytic complexes of the invention, indicated as Catalysts 2a and 2b.
Figure 3:
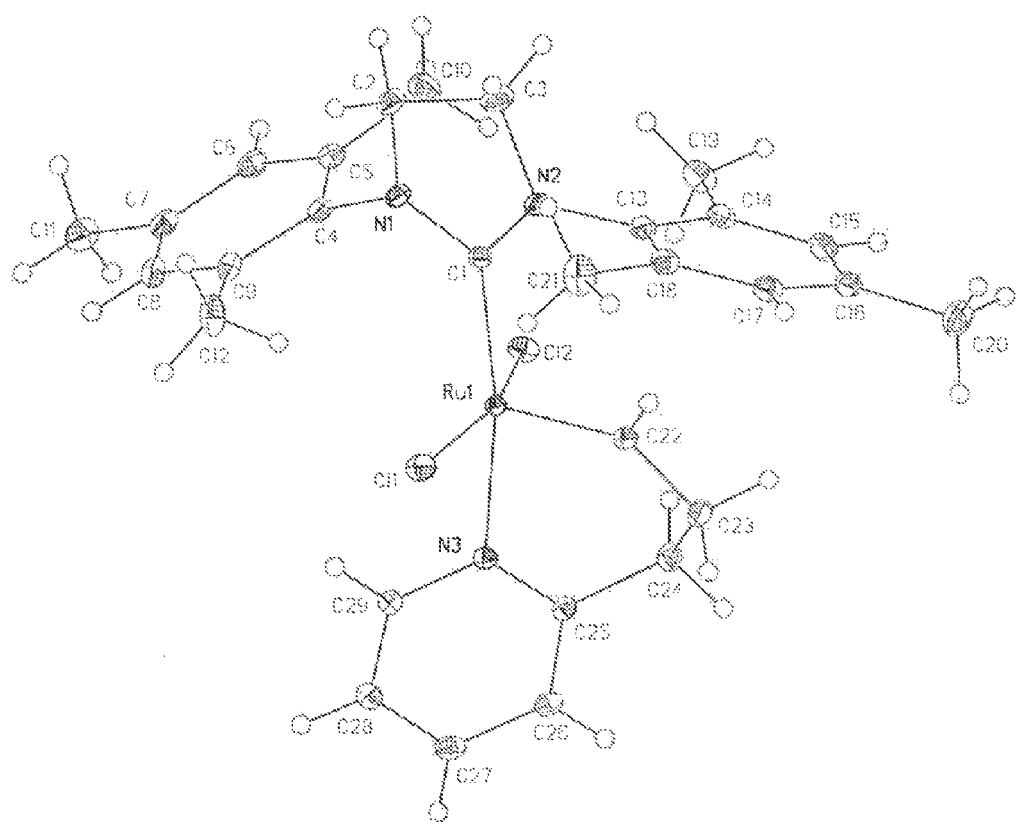

Exemplary catalysts of the invention are 2a and 2b, the molecular structures of which are provided above and in FIG. 2, wherein M is ruthenium, $L^2$ is substituted or unsubstituted pyridyl, $R^1$ and $R^2$ are mesityl(2,4,6-trimethylphenyl), Q is ethylene (II), $X^1$ and $X^2$ are chloride, Y is ethylene (II), m is 1, and n and p are zero. These new catalysts can be prepared by reacting $RuCl_2(sIMes)(PCy_3)(CHPh)$ (Catalyst 1) and 2-(3-butenyl)pyridine in dichloromethane at 40° C. (see Example 1). It has surprisingly found that depending on the reaction time, catalyst 2a can be obtained either in pure form or as a mixture of isomers 2a and 2b. This finding was quite surprising, because the known ruthenium carbene olefin metathesis catalysts typically have a configuration like that of 2a, namely a $C_S$ symmetric square pyramidal geometry where the apical position is occupied by the carbene ligand, and the equatorial positions by two trans anionic ligands and two trans neutral electron donating ligands. In the case of 2b, the complex is of $C_1$ symmetry and contains two equatorial cis anionic ligands and two equatorial cis neutral electron donating ligands. X-ray structures were obtained for 2a and 2b (see ORTEP diagrams in FIGS. 3 and 4). Catalyst 2a can also be prepared by reaction of $(sIMes)(py)_2(Cl)_2Ru=CHPh$ (complex 3) with 1.5 equivalent of 2-(3-butenyl)-pyridine in dichloromethane at room temperature for 30 minutes (Example 2).

Figure 7:
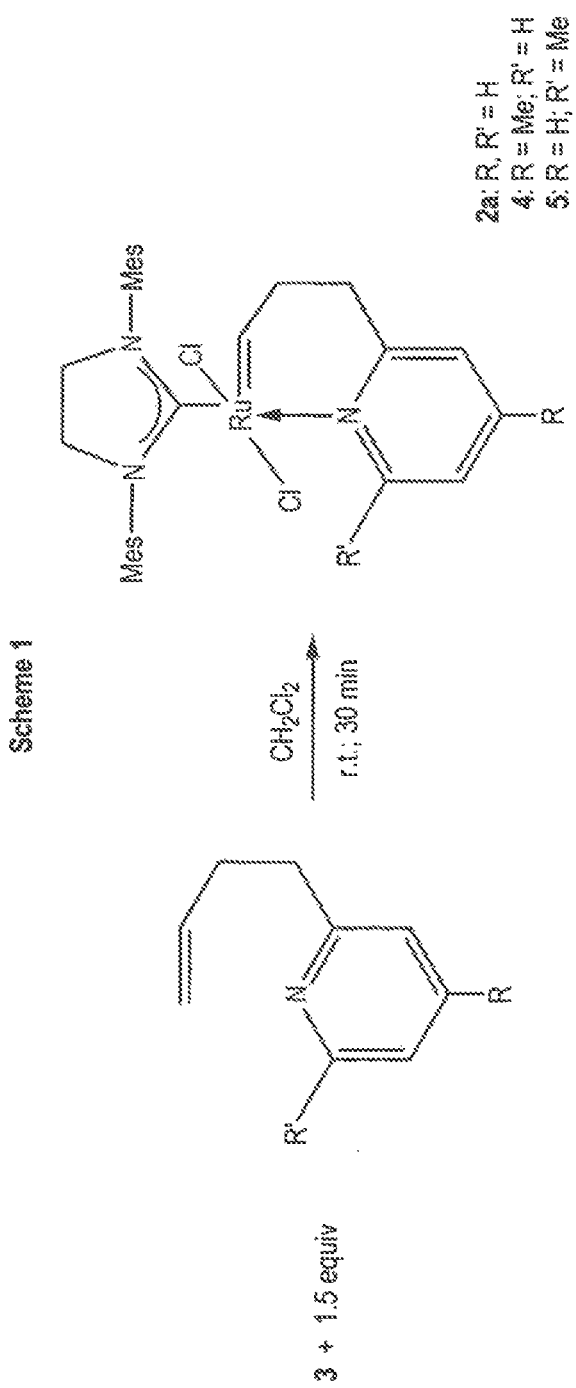
FIG. 7 schematically depicts a method for synthesizing representative catalytic complexes 2a, 4 and 5 of the invention.
Figure 8:
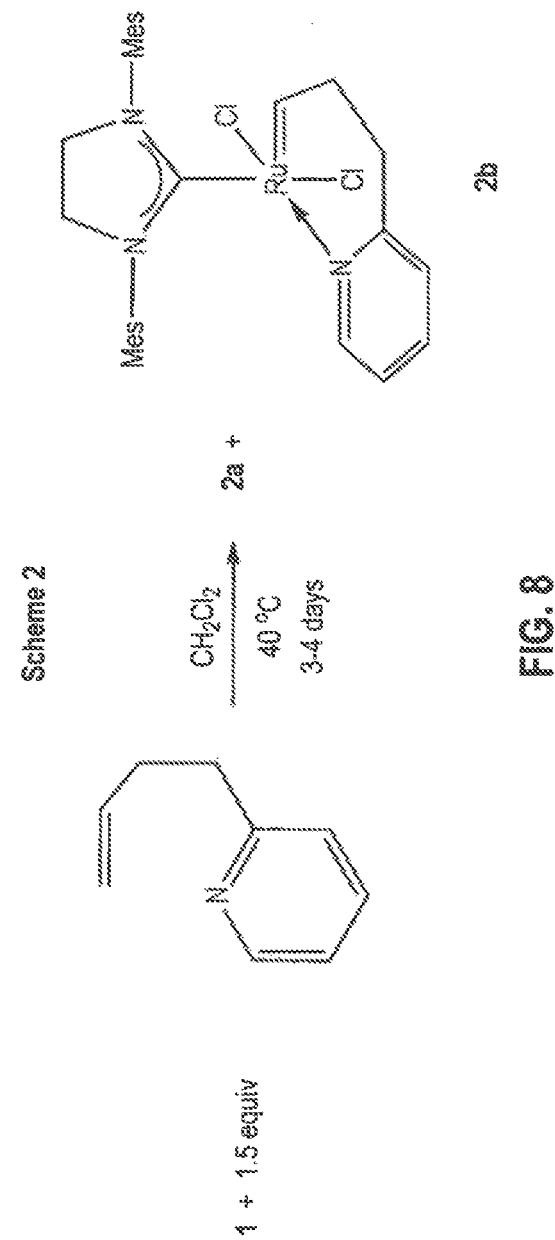
FIG. 8 schematically depicts a method for synthesizing representative catalytic complexes 2b of the invention.

In addition, this method is amenable to the synthesis of complexes $(sIMes)(Cl)_2Ru(CH(CH_2)_2—C,N-2-(4-Me)-C_5H_3N)$ and $Ru(CH(CH_2)_2—C,N-2-(6-Me)-C_5H_3N)$, also shown in FIG. 7.

The catalysts of the invention may be synthesized and used in catalyzing olefin metathesis reactions using the procedures described in the examples herein or variations thereof which will be apparent to one of skill in the art.

Another embodiment of the present invention is a method for the use of the present catalysts, including 2a and 2b, for the metathesis of olefins. Surprisingly, both isomers exhibit large differences in olefin metathesis activity (e.g., in RCM and ROMP). These activity differences enable tuning of the catalyst by simple isomerization of the complex in lieu of the strategies of the prior art, such as utilization of additives or complicated and time-consuming catalyst design involving ligand exchanges. The catalysts may be attached to a solid support; as understood in the field of catalysis, suitable solid supports may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically between a functional group on a support surface and a ligand or substituent on the catalytic complex. The reactions are carried out under conditions normally used in olefin metathesis reactions catalyzed by the Grubbs family of metathesis catalysts. See, e.g., U.S. Pat. Nos. 5,312,940, 5,342,909, 5,831,108, 5,969,170, 6,111,121, and 6,211,391 to Grubbs et al.

As indicated by the results in the examples, various modifications to the basic catalyst structures herein can increase or decrease latency period as desired.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXAMPLE 1

Synthesis of Catalyst 2a

Method A

A 250 mL round bottom Schlenk flask equipped with a stir bar was charged with complex 1, $(sIMes)(PCy_3)(Cl)_2Ru=CHPh$, (10.0 g; 11.8 mmol). The flask was capped, sparged with argon for 15 minutes, and charged with anhydrous $CH_2Cl_2$ (118 mL) via cannula. 2-(3-butenyl)pyridine (2.4 g, 17.7 mmol) was then added via syringe and the reaction mixture was heated to 40° C. for 5-6 hours. The reaction mixture was concentrated to dryness and the residue triturated with degassed, chilled methanol. The solid was collected on a frit and washed with chilled methanol (2×25 mL) to give catalyst 2a, $(sIMes)(Cl)_2Ru(CH(CH_2)_2—C,N-2-C_5H_4N)—C_s$, (5.6 g; 9.4 mmol) as a pale green solid upon drying. Yield: 80%.

EXAMPLE 2

Synthesis of Catalyst 2a

Method B

In the glove box a vial was charged with 2-(3-butenyl)pyridine (24 mg, 0.18 mmol) and $CH_2Cl_2$ (2 mL). Complex 3, $(sIMes)(py)_2(Cl)_2Ru=CHPh$, (86 mg; 0.12 mmol) was then added as a solid and the reaction allowed to stir at room temperature for 30 minutes. The volatiles were removed under vacuum and the residue triturated with hexanes. The solid was collected, washed with hexanes (2×1 mL) and dried under vacuum to give catalyst 2a, $(sIMes)(Cl)_2Ru(CH(CH_2)_2$—$C,N-2-C_5H_4N)$—$C_s$, (60 mg; 0.10 mmol) as a pale green solid upon drying. Yield: 85%. $^1H$ NMR ($CD_2Cl_2$): δ 18.46 (t, $^3J_{HH}$=2.7 Hz, 1H, Ru=CH), 7.64 (d, $^3J_{HH}$=4.8 Hz, 1H, Py), 7.52 (t, $^3J_{HH}$=7.2 Hz, 1H, Py), 7.14 (d, $^3J_{HH}$=7.8 Hz, 1H, Py), 7.07 (s, 4H, Mes), 6.99 (t, $^3J_{HH}$=6.9 Hz, 1H, Py), 4.09 (s, 4H, sIMes), 3.55 (t, $^3J_{HH}$=5.7 Hz, 2H, $CH_2$-Py), 2.50 (s, 12H, Mes-$CH_3$), 2.41 (s, 6H, Mes-$CH_3$), 1.70 (m, 2H, Ru=CH—$CH_2$). $^{13}C\{^1H\}$ NMR ($CD_2Cl_2$): δ 339.18 (Ru=CHCH2), 216.52 (Ru—C(N)$_2$), 162.64, 158.34, 149.54, 138.96, 138.83, 136.96, 129.60, 124.51, 121.82, 54.45, 51.92, 34.30, 21.32, 19.58.

EXAMPLE 3

Conversion of Catalyst 2a to Catalyst 2b

In the glove box, a 0.1 M solution of catalyst 2a in $CD_2Cl_2$ was prepared and transferred to an NMR tube, which was capped and taken out of the glove box. The NMR tube was left in an oil bath at 40° C. and the reaction was monitored by $^1H$ NMR spectroscopy. The ratio of 2b to 2a in the mixture was 30/70 after 24 hours; 60/40 after 48 hours; 70/30 after 72 hours; and 78/22 after 96 hours.

EXAMPLE 4

Conversion of Catalyst 2b to 2a

In the glove box, a 0.1 M solution of catalyst 2b in $CD_2Cl_2$ was prepared and transferred to an NMR tube, which was capped and taken out of the glove box. The NMR tube was left in an oil bath at 40° C. and the reaction was monitored by $^1H$ NMR spectroscopy. The ratio of 2b to 2a in the mixture was 83/17 after 24 hours. $^1H$ NMR spectroscopy also showed that the isomerization of 2b was accompanied with some catalyst decomposition, making it complicated to analyze the reaction mixture beyond 24 hours.

EXAMPLE 5

Synthesis of Catalyst 4

In the glove box, a flask was charged with 2-(3-butenyl)-4-methylpyridine (40 mg, 0.27 mmol) and $CH_2Cl_2$ (5 mL). Complex 3, $(sIMes)(py)_2(Cl)_2Ru=CHPh$, (114 mg; 0.16 mmol) was then added as a solid and the reaction allowed to stir at room temperature for 30 minutes. The volatiles were removed under vacuum and the residue was redissolved in $C_6H_6$ (1 mL) and precipitated with pentane (10 mL). The solid was collected, washed with pentane (3×5 mL) and dried under vacuum to give catalyst 4, $(sIMes)(Cl)_2Ru(CH(CH_2)_2$—$C,N-2-(4-Me)-C_5H_3N)$—$C_s$, (80 mg; 0.13 mmol) as a light brown solid upon drying. Yield: 84%. $^1H$ NMR ($CD_2Cl_2$): δ 18.44 (t, $^3J_{HH}$=3.3 Hz, 1H, Ru=CH), 7.42 (d, $^3J_{HH}$=5.7 Hz, 1H, Py), 7.02 (s, 4H, Mes), 6.95 (s, 1H, Py), 6.80 (d, $^3J_{HH}$=4.2 Hz, 1H, Py), 4.06 (s, 4H, sIMes), 3.46 (t, $^3J_{HH}$=6.0 Hz, 2H, $CH_2$—Py), 2.45 (s, 12H, Mes-$CH_3$), 2.37 (s, 6H, Mes-$CH_3$), 2.27 (s, 3H, Py-$CH_3$), 1.66 (m, 2H, Ru=CH—$CH_2$). $^{13}C\{^1H\}$ NMR ($CD_2Cl_2$): δ 339.16 (Ru=CHCH2), 216.91 (Ru—C(N)$_2$), 161.97, 148.96, 148.87, 138.99, 138.83, 129.63, 125.43, 122.98, 54.62, 51.95, 34.13, 21.35, 21.01, 19.64.

EXAMPLE 6

Synthesis of Catalyst 5

In the glove box, a flask was charged with 2-(3-butenyl)-6-methylpyridine (50 mg, 0.34 mmol) and $CH_2Cl_2$ (5 mL). Complex 3, $(sIMes)(py)_2(Cl)_2Ru=CHPh$, (98 mg; 0.14 mmol) was then added as a solid and the reaction allowed to stir at room temperature for 30 minutes. The volatiles were removed under vacuum and the residue was redissolved in $C_6H_6$ (1 mL) and precipitated with pentane (10 mL). The solid was collected, washed with pentane (3×5 mL) and dried under vacuum to give catalyst 5, $(sIMes)(Cl)_2Ru(CH(CH_2)_2$—$C,N-2-(6-Me)-C_5H_3N)$—$C_s$, (57 mg; 0.094 mmol) as a light brown solid upon drying. Yield: 69%. $^1H$ NMR ($CD_2Cl_2$): δ 18.33 (t, $^3J_{HH}$=3.6 Hz, 1H, Ru=CH), 7.34 (t, $^3J_{HH}$=7.5 Hz, 1H, Py), 7.03 (s, 4H, Mes), 6.97 (d, $^3J_{HH}$=7.8 Hz, 1H, Py), 6.75 (d, $^3J_{HH}$=7.8 Hz, 1H, Py), 4.05 (m, 4H, sIMes), 2.91 (m, 4H, Ru=CH—$CH_2$—$CH_2$—Py), 2.61 (br s, 6H, Mes-$CH_3$), 2.37 (s, 6H, Mes-$CH_3$), 2.31 (br s, 6H, Mes-$CH_3$), 2.01 (s, 3H, Py-$CH_3$). $^{13}C\{^1H\}$ NMR ($CD_2Cl_2$): δ 343.54 (Ru=CHCH2), 218.21 (Ru—C(N)$_2$), 160.62, 160.55, 140.45, 139.29, 138.73, 137.88, 136.65, 129.79, 128.82, 123.03, 122.13, 52.04, 51.24, 34.66, 32.20, 22.86, 21.76, 21.34, 20.37, 18.51.

It should be noted that the $^1H$ NMR spectra for catalysts 2a, 4 and 5 are consistent with complexes of $C_s$ symmetry, where the resonances for each of the para methyl groups of the mesityl rings, the ortho methyl groups of the same rings and the ethylene bridge of the sIMes ligand appear as singlets [the $^1H$ NMR singlets described are consistent with a $C_s$ symmetry and free rotation of the sIMes ligand around the Ru—C bond (on the NMR time-scale)]. The alkylidene proton resonances near 18 ppm appear as triplets due to coupling to the methylene protons ($^3J_{HH}$=2.7-3.6 Hz).

EXAMPLE 7

Synthesis of Catalyst 2b

A 220 mL round bottom Schlenk flask equipped with a stir bar was charged with complex 1, $(sIMes)(PCy_3)(Cl)_2Ru=CHPh$, (5.0 g; 5.9 mmol). The flask was capped, sparged with argon for 15 minutes, and charged with anhydrous $CH_2Cl_2$ (60 mL) via cannula. 2-(3-butenyl)pyridine (1.2 g, 8.9 mmol) was then added via syringe and the reaction mixture was heated to 40° C. for 3-4 days. The reaction mixture was concentrated to dryness and the residue triturated with degassed, chilled methanol (15 mL). The solid was collected on a frit and washed with methanol (2×10 mL) to give catalyst 2b, $(sIMes)(Cl)_2Ru(CH(CH_2)_2$—$C,N-2-C_5H_4N)$—$C_1$, (1.3 g; 2.2 mmol) as an orange-brown solid upon drying. Yield: 37%. $^1H$ NMR ($CD_2Cl_2$): δ 19.14 (t, $^3J_{HH}$=3.3 Hz, 1H, Ru=CH), 7.54 (d, $^3J_{HH}$=7.8 Hz, 1H, Py), 7.49 (t, $^3J_{HH}$=5.1 Hz, 1H, Py), 7.25 (s, 1H, Mes), 7.06 (s, 1H, Mes), 7.03 (d, $^3J_{HH}$=7.8 Hz, 1H, Py), 6.90 (s, 1H, Mes), 6.88 (s, 1H, Mes), 6.81 (t, $^3J_{HH}$=6.6 Hz, 1H, Py), 4.15 (m, 2H, sIMes), 3.90 (m, 2H, sIMes), 3.00 (m, 2H, CH$_2$—Py), 2.88 (s, 3H, Mes-CH$_3$), 2.69 (s, 3H, Mes-CH$_3$), 2.40 (s, 3H, Mes-CH$_3$), 2.34 (s, 3H, Mes-CH$_3$), 1.96 (s, 3H, Mes-CH$_3$), 1.78 (m, 1H, Ru=CH—CH$_2$), 1.45 (s, 3H, Mes-CH$_3$), 1.21 (m, 1H, Ru=CH—CH$_2$). $^{13}$C{$^1$H} NMR (CD$_2$Cl$_2$): δ 319.04 (Ru=CHCH2), 218.94 (Ru—C(N)$_2$), 161.71, 154.02, 139.51, 138.94, 138.32, 137.90, 135.57, 134.97, 132.96, 130.26, 129.53, 129.34, 129.16, 128.65, 122.94, 120.00, 50.54, 49.23, 34.87, 20.52, 20.27, 19.25, 18.92, 18.39, 17.56.

Catalyst 2b appears as a ruthenium carbene of C$_1$ symmetry, displaying six nonequivalent methyl groups on the mesityl rings, four nonequivalent protons on the ethylene bridge of the sIMes ligand and 4 nonequivalent protons on the ethylene bridge of the pyridyl ligand in the $^1$H NMR spectrum. The carbene resonance of 2b also appears as a triplet (619.14 ppm; $^3J_{HH}$=3.3 Hz). Pure isolated 2a, dissolved in CD$_2$Cl$_2$ (0.1 M), is slowly converted to a 22:78 mixture of 2a:2b at 40° C. over the course of 96 hours and pure isolated 2b forms a similar mixture under the same conditions. It may therefore be concluded that 2a and 2b are isomers in equilibrium where 2b is the thermodynamically favored species and K$_{eq}$=0.28. Attempts to measure the kinetics of the approach to equilibrium were hampered by a decomposition process concurrent with the 2a↔2b isomerization process.

Figure 9:
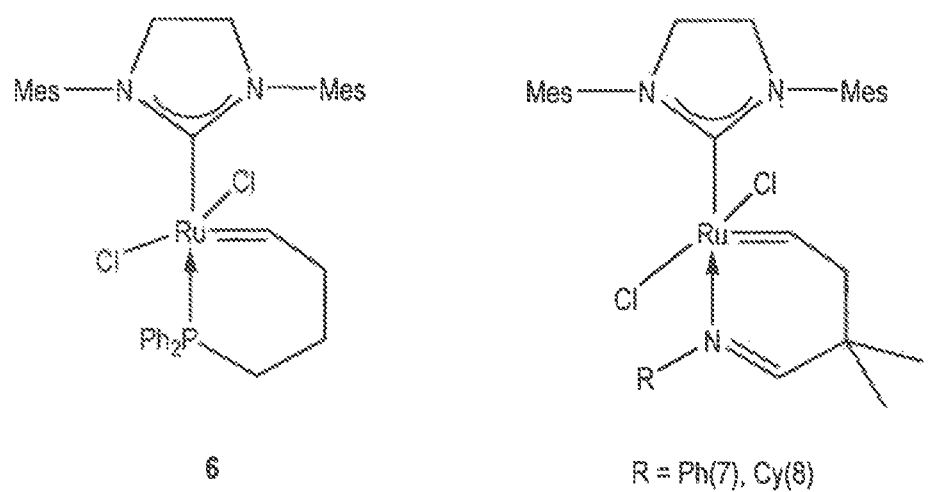
FIG. 9 provides the molecular structure of additional representative catalytic complexes of the invention.
Figure 10:
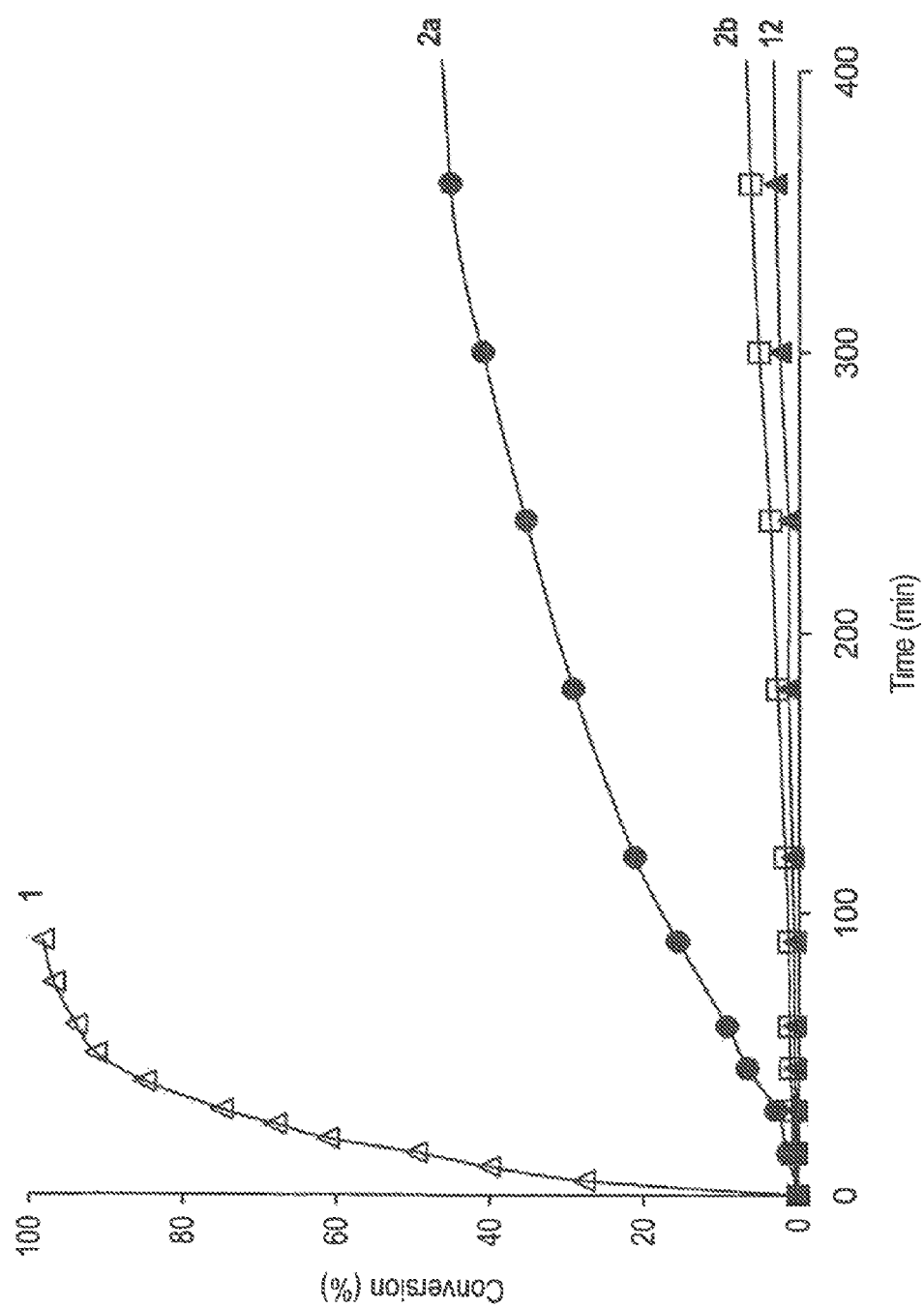
FIG. 10 illustrates the percent of reactant converted versus time for the RCM reaction of diethyldiallyl malonate using catalysts 1, 2a, 2b and 12, as described in Example 15.

Crystals suitable for X-ray analysis were obtained for catalysts 2a and 2b (ORTEP views of 2a and 2b are shown in FIGS. 9 and 10, respectively). Both complexes display square pyramidal geometries, where the chloride, pyridine and NHC ligands occupy the equatorial positions and the alkylidene occupies the axial position. In 2a, the chloride ligands are trans one to another [Cl(1)-Ru(1)-Cl(2)=164.41(1)] as are the neutral ligands [C(1)-Ru(1)-N(3)=170.21(4)]. This geometry is typical for ruthenium olefin metathesis catalysts and is consistent with the $^1$H NMR spectrum of 2a. On the other hand, 2b possesses cis chloride ligands (Cl(1)-Ru(1)-Cl(2)=85.93(2)) and cis neutral ligands (C(1)-Ru(1)-N(3)=98.04(8)), which explain the C$_1$ symmetry deduced from the spectroscopic data. This type of ligand arrangement is relatively rare for ruthenium carbene complexes, although it has been observed in a few cases [ruthenium complexes containing chelating bisphosphine ligands and cis chlorides have been described: see, e.g., Hansen et al. (1999) *Angew. Chem., Int. Ed.* 38, 1273-1276; Hansen et al. (1999) *Chem. Eur. J.* 5, 557-566; Volland et al. (2001) *Organomet. Chem.* 617, 288-291; Nieczypor et al. (2001). *J. Organomet. Chem.* 625, 58-66; Priihs et al. (2004) *Organometallics* 23, 280-287; Slugovc et al. (2004) *Organometallics*, 23, 3622-3626. A related complex with cis neutral ligands and cis anionic pentafluorophenoxide ligands has been reported: see Conrad et al. (2003) *Organometallics* 22, 3634-3636; a related vinylcarbene ruthenium complex containing cis chlorides has also been reported: see Trnka et al. (2001) *Organometallics* 20, 3845-3847]. The Ru(1)-N(3) distance of 2.1355(9) Å in 2a is significantly longer than that of 2.098(2) Å in 2b, due to the trans influence of the NHC ligand. Similarly, the Ru(1)-Cl(2) distance in 2b (2.3883(6) Å) is longer than that in 2a (2.3662(3) Å).

EXAMPLE 8

Synthesis of Catalyst Ru(C4-PPh$_2$) (6)

In the glove box, a flask was charged with (4-pentenyl) diphenyl phosphine (49 mg, 0.19 mmol) and CH$_2$Cl$_2$ (5 mL). Catalyst 3, RuCl$_2$(sIMes)(py)$_2$(CHPh), (127 mg; 0.17 mmol) was then added as a solid and the reaction allowed to stir at room temperature for 30 minutes. The volatiles were removed under vacuum and the residue was washed with pentane (2×2 mL). The solid was redissolved in CH$_2$Cl$_2$ (5 mL) and heated to 40° C. for 12 h, after which volatiles were removed under vacuum. The solid was purified by column chromatography (5% Et$_2$O/pentane, then 25% Et$_2$O/pentane) and dried under vacuum to give catalyst 6. (59 mg; 0.082 mmol) as a light brown solid upon drying. Yield: 47%. $^1$H NMR (CD$_2$Cl$_2$): δ 18.60 (td, $^3J_{HH}$=6.3 Hz, $^3J_{PH}$=1.8 Hz, 1H, Ru=CH), 7.30 (m, 2H, PPh$_2$), 7.18 (m, 4H, PPh$_2$), 6.97 (s, 4H, Mes), 6.89 (m, 4H, PPh$_2$), 4.07 (m, 4H, sIMes), 2.79 (q, $^3J_{HH}$=6.3 Hz, 2H, Ru=CH—CH$_2$—CH$_2$), 2.53 (s, 6H, Mes-CH$_3$), 2.39 (s, 6H, Mes-CH$_3$), 2.35 (s, 6H, Mes-CH$_3$), 2.30 (m, 2H, CH$_2$—CH$_2$—PPh$_2$), 1.53 (m, 2H, CH$_2$—CH$_2$—CH$_2$—PPh$_2$). $^{31}$P{$^1$H} NMR (CD$_2$Cl$_2$): δ 45.49.

EXAMPLE 9

Synthesis of Catalyst Ru(Ph-Im) (7)

In the glove box, a flask was charged with catalyst 3, RuCl$_2$(sIMes)(py)$_2$(CHPh), (154.7 mg; 0.21 mmol) and CH$_2$Cl$_2$ (5 mL). (2,2-dimethyl-pent-4-enylidene)-phenylamine (60 mg, 0.32 mmol) was then added via syringe and the reaction allowed to stir at room temperature for 15 minutes. The volatiles were removed under vacuum and the residue was washed with pentane (2×2 mL). The solid was redissolved in C$_6$H$_6$ (2 mL) and precipitated with pentane (20 mL). The solid was collected, washed with pentane (3×5 mL) and dried under vacuum to give catalyst 7 (115.6 mg; 0.18 mmol) as an olive green solid upon drying. Yield: 83%. $^1$H NMR (CD$_2$Cl$_2$): δ 18.80 (t, $^3J_{HH}$=5.4 Hz, 1H, Ru=CH), 7.64 (s, 1H, C(=N)H), 7.2-6.9 (m, 9H, Ar—H), 4.01 (s, 4H, sIMes), 3.02 (d, $^3J_{HH}$=5.4 Hz, 2H, Ru=CH—CH$_2$—CMe$_2$), 2.5-2.3 (m, 18H, Mes-CH$_3$), 1.07 (s, 6H, CMe$_2$). $^{13}$C{$^1$H} NMR (CD$_2$Cl$_2$): δ 345.10 (Ru=CHCH2), 218.03 (Ru—C(N)$_2$), 176.96 (Ru—N=C), 149.63, 138.81, 129.82, 129.40, 127.12, 122.48, 64.30, 51.82, 42.69, 26.89, 21.46, 19.28.

EXAMPLE 10

Synthesis of Catalyst Ru(Cy-Im) (8)

In the glove box, a flask was charged with catalyst 3, RuCl$_2$(sIMes)(py)$_2$(CHPh), (191.5 mg; 0.26 mmol) and CH$_2$Cl$_2$ (5 mL). (2,2-dimethyl-pent-4-enylidene)-cyclohexyl-amine (74 mg, 0.38 mmol) was then added via syringe and the reaction allowed to stir at room temperature for 15 minutes. The volatiles were removed under vacuum and the residue was washed with pentane (2×2 mL). The solid was redissolved in C$_6$H$_6$ (2 mL) and precipitated with pentane (20 mL). The solid was collected, washed with pentane (3×5 mL) and dried under vacuum to give catalyst 8 (146.1 mg; 0.22 mmol) as an olive green solid upon drying. Yield: 84%. $^1$H NMR (CD$_2$Cl$_2$): δ 18.56 (t, $^3J_{HH}$=5.4 Hz, 1H, Ru=CH), 7.41 (s, $^3J_{HH}$=5.4 Hz, 1H, C(=N)H), 7.00 (br s, 4H, Mes), 4.00 (br s, 4H, sIMes), 2.96 (d, $^3J_{HH}$=5.7 Hz, 2H, Ru=CH—CH$_2$—CMe$_2$), 2.7-2.2 (br m, 12H, Mes-CH$_3$), 2.34 (s, 6H, Mes-CH$_3$), 1.7-0.8 (m, 11H, Cy), 0.91 (s, 6H, CMe$_2$).

EXAMPLE 11

Synthesis of Catalyst Ru(iPr-Im) (9)

In the glove box, a flask was charged with Catalyst 3, RuCl$_2$(sIMes)(py)$_2$(CHPh) (239 mg; 0.33 mmol) and CH$_2$Cl$_2$ (5 mL). (2,2-dimethyl-pent-4-enylidene)-isopropyl-amine (76 mg, 0.38 mmol) was then added via syringe and the reaction allowed to stir at room temperature for 15 minutes. The volatiles were removed under vacuum, the residue was redissolved in $C_6H_6$ (2 mL) and precipitated with pentane (20 mL). The solid was collected, washed with pentane (3×5 mL) and dried under vacuum to give catalyst 3 (162 mg; 0.26 mmol) as a pale green solid upon drying. Yield: 80%. $^1$H NMR ($CD_2Cl_2$): δ 18.58 (t, $^3J_{HH}$=5.4 Hz, 1H, Ru=CH), 7.41 (d, $^3J_{HH}$=1.5 Hz, 1H, C(=N)H), 6.99 (s, 4H, Mes), 4.02 (br s, 4H, sIMes), 3.32 (sept. d, $J_{HH}$=6.6, 1.5 Hz, 1H, NCH($CH_3$)$_2$), 2.96 (d, $^3J_{HH}$=5.4 Hz, 2H, Ru=CH—$CH_2$—$CMe_2$), 2.42 (br s, 12H, Mes-$CH_3$), 2.34 (s, 6H, Mes-$CH_3$), 0.92 (s, 6H, $CMe_2$). 0.90 (d, $^3J_{HH}$=6.9 Hz, 6H, NCH($CH_3$)$_2$). $^{13}$C{$^1$H} NMR ($CD_2Cl_2$): δ 345.17 (Ru=CHCH2), 219.54 (Ru—C(N)$_2$) 173.68, 138.91, 129.74, 64.21, 60.78, 51.60, 42.51, 26.96, 22.47, 21.36, 19.36 (br).

EXAMPLE 12

Synthesis of Catalyst Ru(tBu-Im) (10)

In the glove box, a flask was charged with Catalyst 3, $RuCl_2$(sIMes)(py)$_2$(CHPh) (188 mg; 0.26 mmol) and $CH_2Cl_2$ (5 mL). (2,2-dimethyl-pent-4-enylidene)-tert-butyl-amine (56 mg, 0.34 mmol) was then added via syringe and the reaction allowed to stir at room temperature for 15 minutes. The volatiles were removed under vacuum, the residue was redissolved in $C_6H_6$ (2 mL) and precipitated with pentane (20 mL). The solid was collected, washed with pentane (3×5 mL) and dried under vacuum to give catalyst 10 (91 mg; 0.14 mmol) as pale green solid upon drying. Yield: 56%. $^1$H NMR ($CD_2Cl_2$): δ 18.37 (t, $^3J_{HH}$=5.7 Hz, 1H, Ru=CH), 7.43 (s, 1H, C(=N)H), 7.04-6.94 (m, 4H, Mes), 4.10-3.86 (m, 4H, sIMes), 3.08 (d, $^3J_{HH}$=5.4 Hz, 2H, Ru=CH—$CH_2$—$CMe_2$), 2.59 (br s, 6H, Mes-$CH_3$), 2.34 (s, 6H, Mes-$CH_3$), 2.26 (br s, 6H, Mes-$CH_3$), 1.0 (s, 9H, $NCMe_3$), 0.91 (s, 6H, $CMe_2$). $^{13}$C{$^1$H} NMR ($CD_2Cl_2$): δ 345.22 (Ru=CHCH2), 219.82 (Ru—C(N)$_2$), 172.97, 139.83, 139.13, 138.55, 137.92, 136.09, 129.83, 129.74, 64.05, 63.66, 51.75, 51.27, 43.02, 25.89, 26.77, 21.37, 20.21, 18.58.

EXAMPLE 13

Synthesis of Catalyst Ru(Me-Im) (11)

In the glove box, a flask was charged with Catalyst 3, $RuCl_2$(sIMes)(py)$_2$(CHPh) (143 mg; 0.20 mmol) and $CH_2Cl_2$ (5 mL). (2,2-dimethyl-pent-4-enylidene)-methyl-amine (30 mg, 0.24 mmol) was then added via syringe and the reaction allowed to stir at room temperature for 30 minutes. The volatiles were removed under vacuum, the residue was redissolved in $C_6H_6$ (2 mL) and precipitated with pentane (20 mL). The solid was collected, washed with pentane (3×5 mL) and dried under vacuum to give catalyst 11 (93 mg; 0.16 mmol) as a green-brown solid upon drying. Yield: 84%. $^1$H NMR ($CD_2Cl_2$): δ 18.80 (t, $^3J_{HH}$=5.1 Hz, 1H, Ru=CH), 7.42 (m, 1H, C(=N)H), 7.00 (br s, 4H, Mes), 4.05 (s, 4H, sIMes), 2.73 (d, $^4J_{HH}$=1.2 Hz, 3H, C=NMe), 2.69 (d, $^3J_{HH}$=5.1 Hz, 2H, Ru=CH—$CH_2$—$CMe_2$), 2.41 (s, 12H, Mes-$CH_3$), 2.34 (s, 6H, Mes-$CH_3$), 0.93 (s, 6H, $CMe_2$). $^{13}$C{$^1$H} NMR ($CD_2Cl_2$): δ 342.54 (Ru=CHCH2), 218.93 (Ru—C(N)$_2$), 175.29, 139.04, 138.87, 136.52, 129.61, 64.46, 51.85, 46.76, 41.83, 26.88, 21.37, 19.56.

EXAMPLE 14

Synthesis of Catalyst 12

In the glove box, a flask was charged with Catalyst 3, $RuCl_2$(sIMes)($PCy_3$)(CHPh) (5.0 g; 5.9 mmol) and $CH_2Cl_2$ (60 mL). Ortho-(N,N)-dimethylaminostyrene (1.7 g; 11.8 mmol; 2 equiv), prepared according to a literature procedure (see J. Chem. Soc. 1958, 2302), was added and the reaction mixture was stirred at 40° C. for 24 hours under inert atmosphere. The volatiles were removed under vacuum, the residue was triturated with methanol (10 mL) and the solid collected on a fritted glass filtration funnel. The solid was then washed with additional methanol (2×10 mL) and hexanes (2×10 mL) before it was dried under vacuum to give catalyst 12 (2.8 g; 4.6 mmol) as a green solid. Yield: 78%. $^1$H NMR ($CD_2Cl_2$): δ 16.85 (s, 1H, Ru=CH), 7.58 (t, 1H, Ar), 7.22 (d, 1H, Ar), 7.10 (t, 1H, Ar), 7.08 (s, 4H, Mes), 6.82 (d, 1H, Ar), 4.10 (br s, 4H, $CH_2CH_2$), 2.50 (s, 6H, Mes-$CH_3$), 2.48 (s, 12H, Mes-$CH_3$), 2.40 (s, 6H, $NMe_2$).

EXAMPLE 15

Activity of Catalysts 1, 2a, 2b and 12

RCM of Diethylallyl Malonate

The ring-closing metathesis of diethyldiallyl malonate was used as a test reaction to compare the activity of the different catalysts. For the comparison of catalysts 1, 2a, 2b and 12: 1 mol % of catalyst was added to a 0.1 M solution of diethyldiallyl malonate in dichloromethane and the reaction was allowed to proceed at 25° C. and was monitored by gas-chromatography (FIG. 10). As shown in FIG. 10, 2a is much slower than 1 (<20% conversion after 100 min versus ~100% conversion, respectively, under the conditions used), 2b is much slower than 2a (<2% conversion after 100 min under the conditions used), and 12 is much slower than 2b.

EXAMPLE 16

Activity of Catalysts 2a, 4 and 5

RCM of Diethylallyl Malonate

Figure 4:
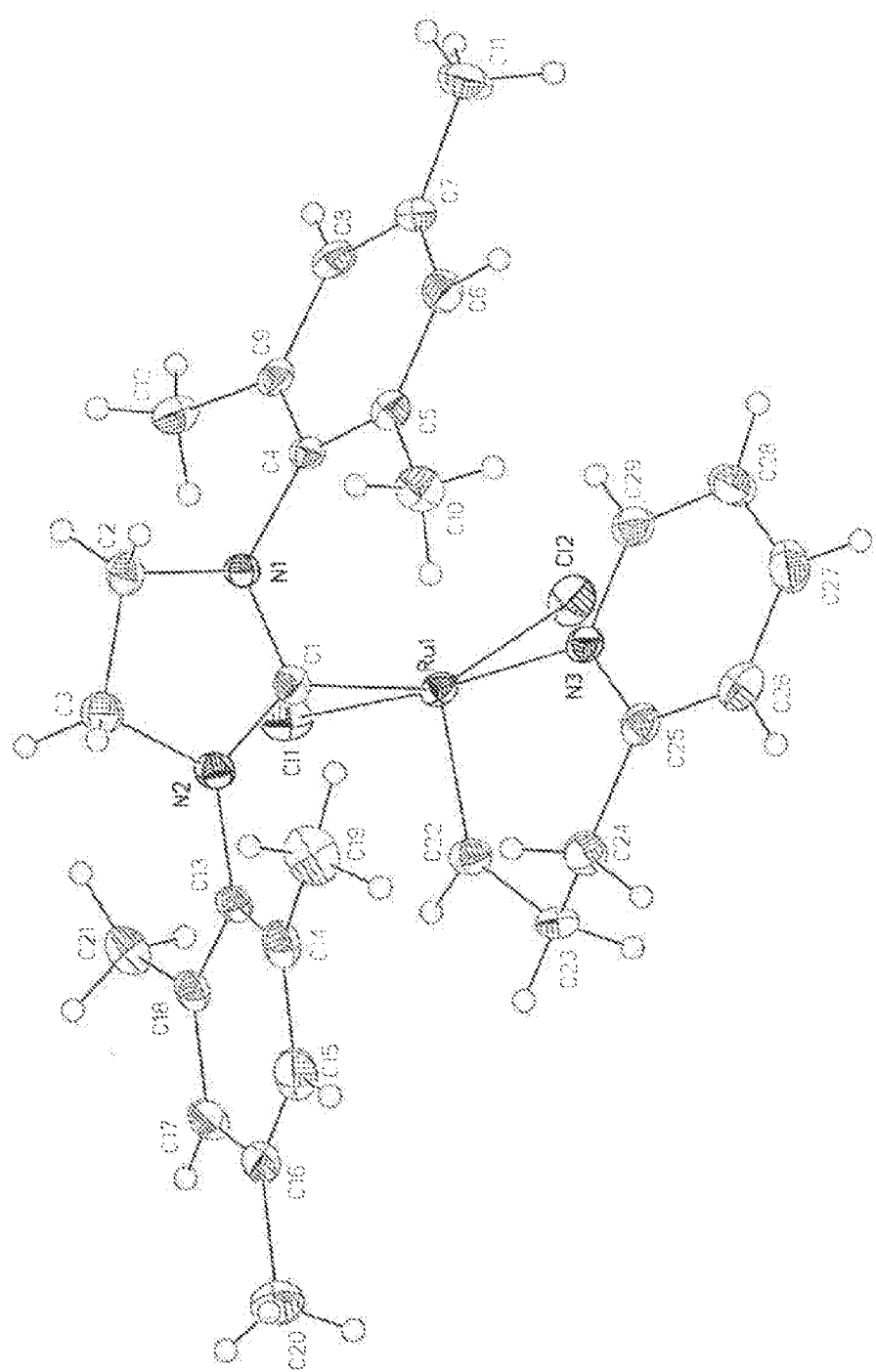
FIG. 4 depicts an ORTEP drawing of the X-ray crystal structure of Catalyst 2b.
Figure 5:
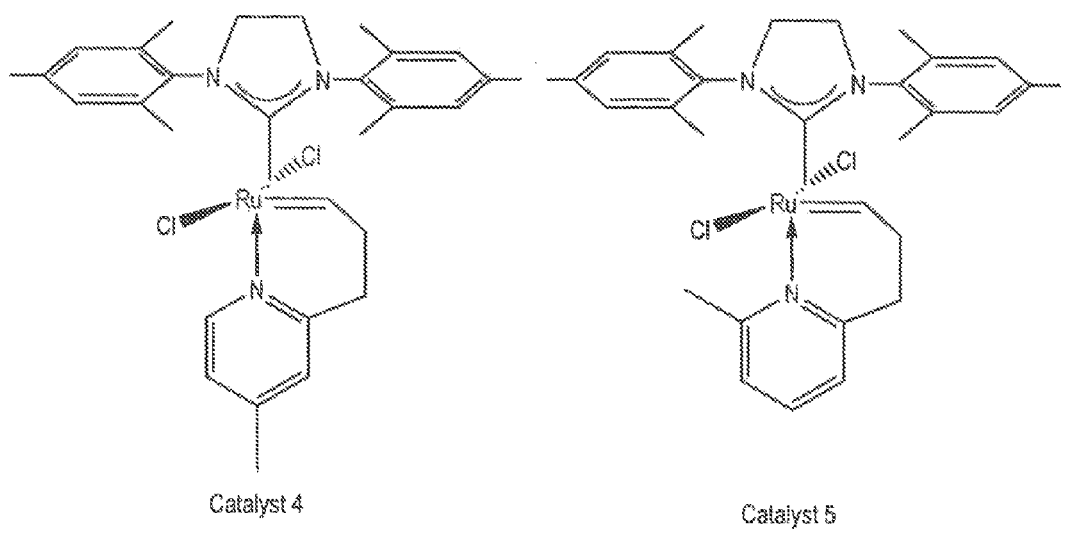
FIG. 5 provides the molecular structures of two representative catalytic complexes of the invention, indicated as Catalysts 4 and 5.
Figure 6:
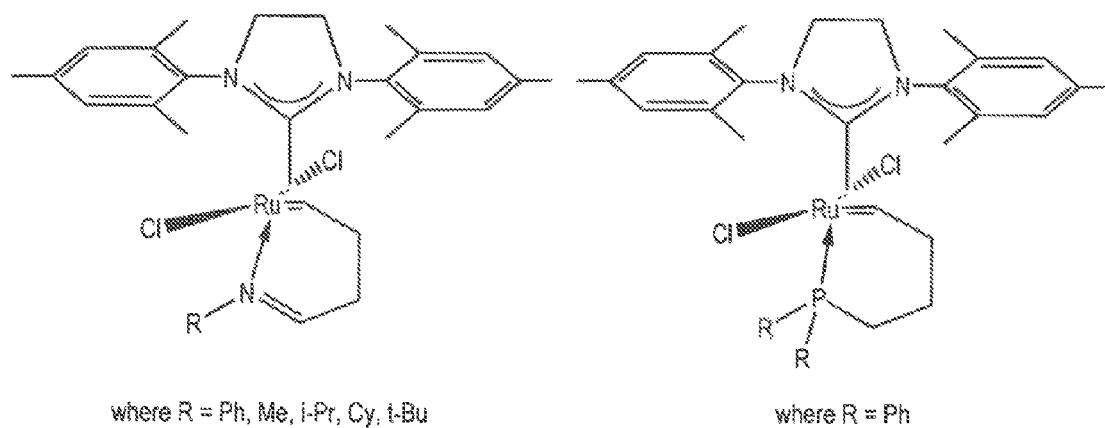
FIG. 6 provides the molecular structures of additional representative catalytic complexes of the invention.
Figure 11:
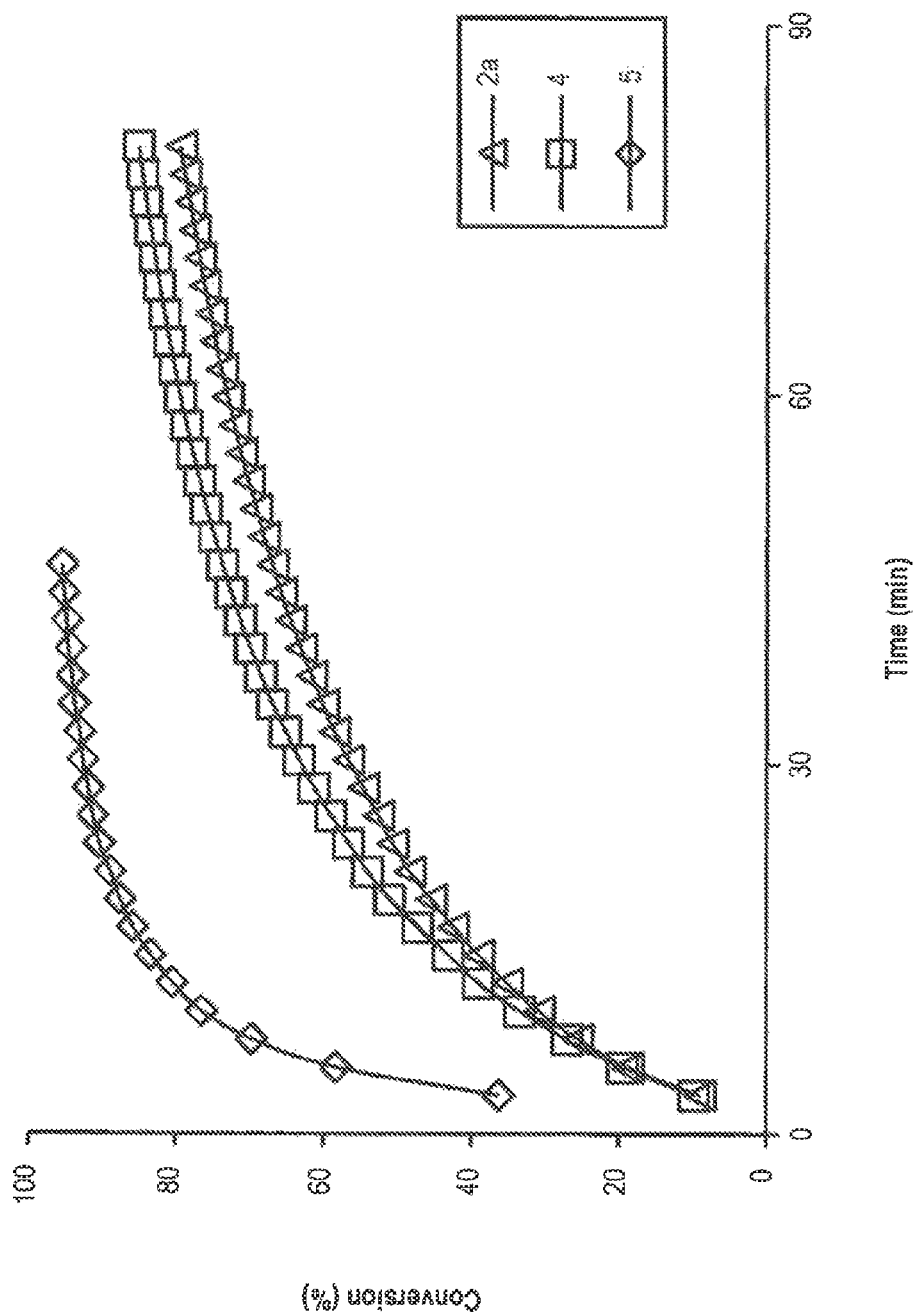
FIG. 11 illustrates the percent of reactant converted versus time for the RCM reaction of diethyldiallyl malonate using catalysts 2a, 4 and 5, as described in Example 16.

The ring-closing metathesis of diethyldiallyl malonate was used as a test reaction to compare the activity of catalysts 2a, 4 and 5. In the dry box, 2.5 mol % of catalyst (0.0052 mmol) was dissolved in $C_6D_6$ (0.65 mL) in an NMR tube fitted with a teflon septum screw-cap. The resulting solution was allowed to equilibrate in the NMR probe at 40° C. Diethyl-diallyl malonate (50 μL, 0.207 mmol, 0.30 M) was injected into the NMR tube neat and the reaction was monitored by $^1$H NMR spectroscopy (FIG. 11). The olefinic resonances integrals of the product relative to that of the starting material were measured with the residual protio solvent peak used as an internal standard. As shown in FIG. 11, 2a and 4 show similar reactivity in RCM, but 5 proved to initiate faster than 2a and 4, presumably due to steric crowding of the ortho methyl group on the pyridine ligand.

EXAMPLE 17

Activity of Catalysts 2a, 7 and 8

RCM of Diethylallyl Malonate

Figure 12:
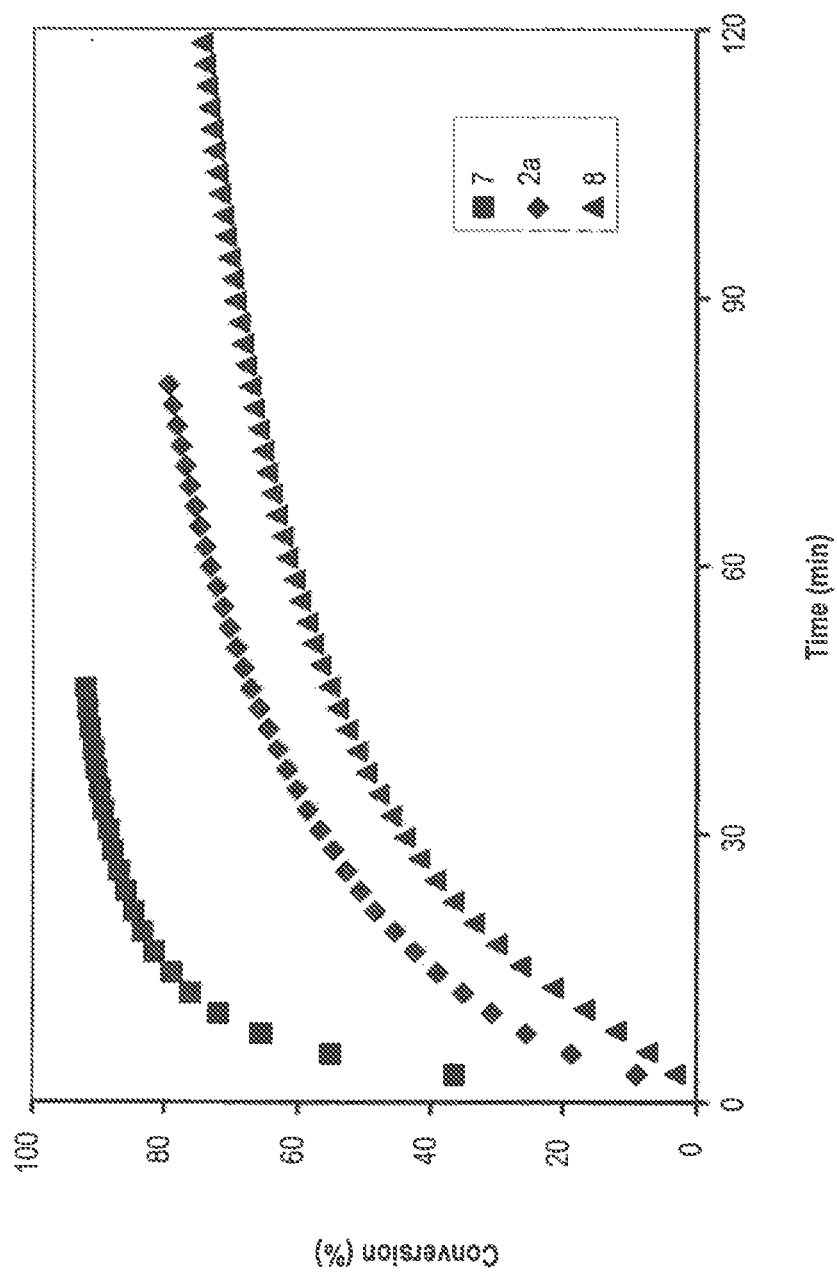
FIG. 12 illustrates the percent of reactant converted versus time for the RCM reaction of diethyldiallyl malonate using catalysts 2a, 7 and 8, as described in Example 17.

As in Example 16, the ring-closing metathesis of diethyl-diallyl malonate was used as a test reaction to compare the activity of catalysts 2a, 7 and 8. In the dry box, 2.5 mol % of catalyst (0.0052 mmol) was dissolved in $C_6D_6$ (0.65 mL) in an NMR tube fitted with a teflon septum screw-cap. The resulting solution was allowed to equilibrate in the NMR probe at 40° C. Diethyldiallyl malonate (50 µL, 0.207 mmol, 0.30 M) was injected into the NMR tube neat and the reaction was monitored by $^1$H NMR spectroscopy (FIG. 12). The olefinic resonances integrals of the product relative to that of the starting material were measured with the residual protio solvent peak used as an internal standard. As shown in FIG. 12, catalyst 7 is faster than 2a in RCM, while 8 is slower than 2a.

Figure 13:
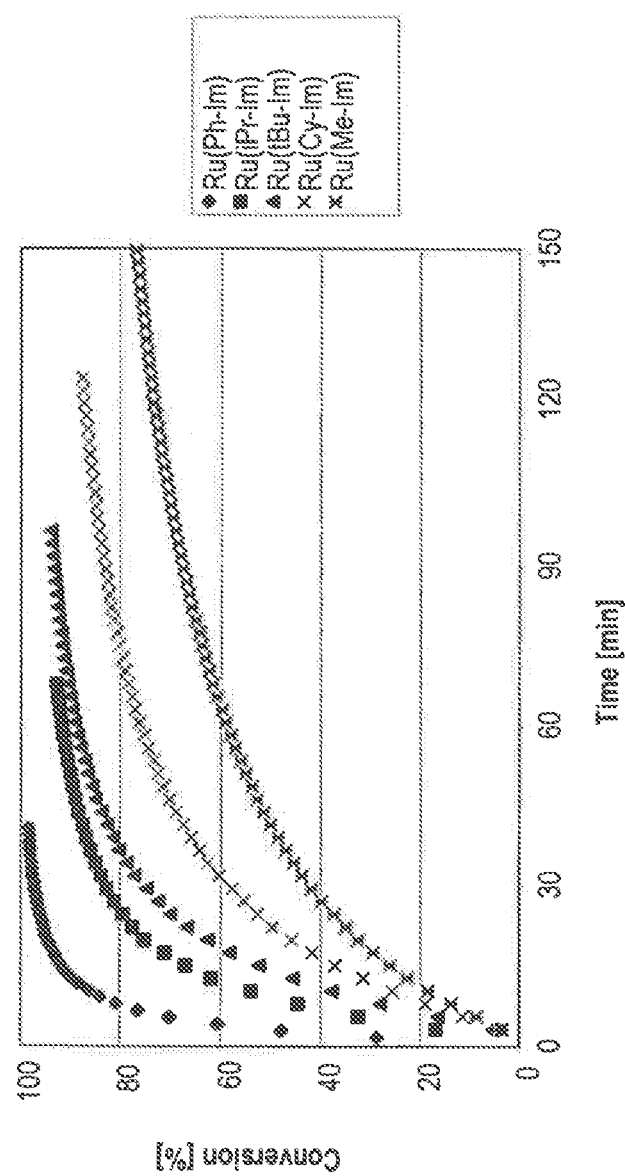
FIG. 13 illustrates the percent of reactant converted versus time for the RCM reaction of diethyldiallyl malonate using catalysts 7, 8, 9, 10, and 11, as also described in Example 17.

The foregoing test reaction was then re-run to compare catalysts 7, 8, 9, 10, and 11, with the results given in FIG. 13.

EXAMPLE 18

Activity of Catalysts 6 and 8

RCM of Diethylallyl Malonate

Figure 14:
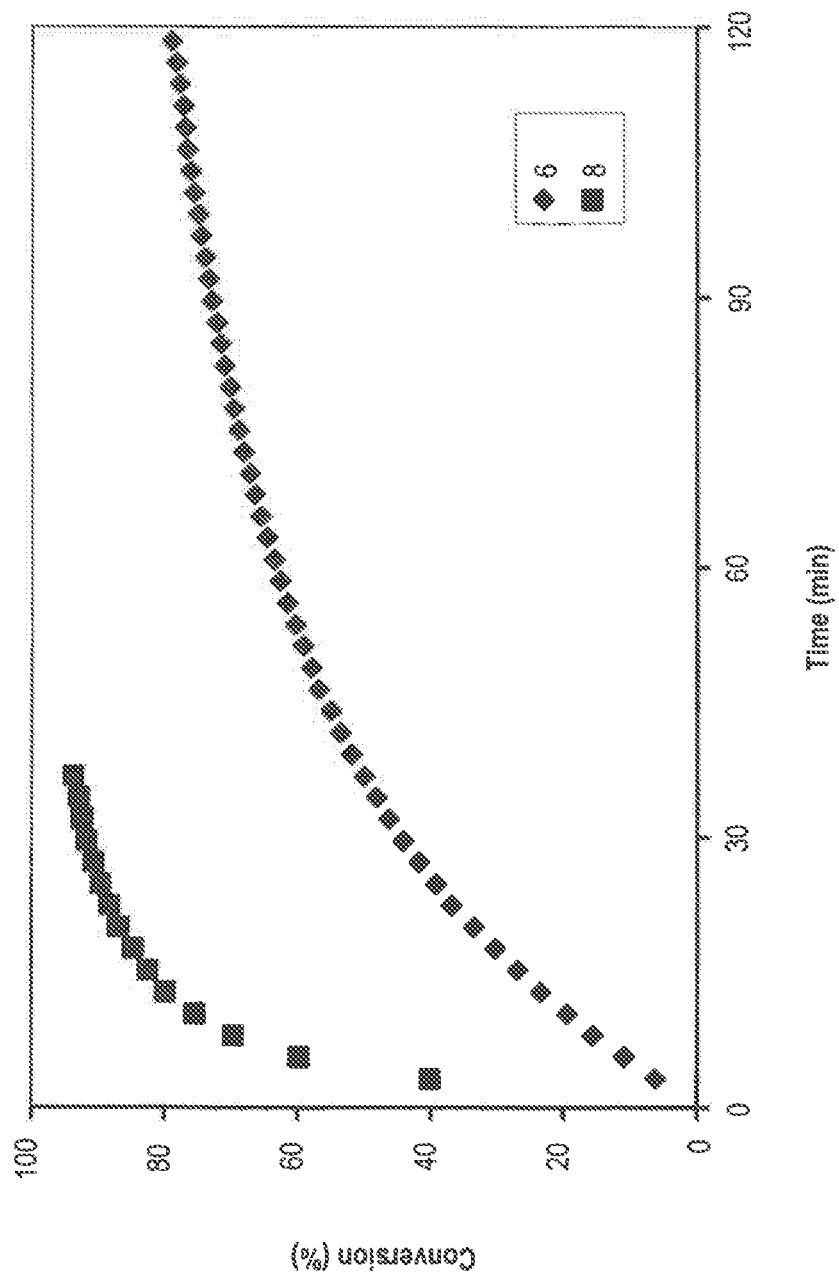
FIG. 14 provides the exotherms for the RCM reaction of diethyldiallyl malonate to assess the activity of catalysts 6 and 8, as described in Example 18.

As in Example 16, the ring-closing metathesis of diethyldiallyl malonate was used as a test reaction to compare the activity of catalysts 6 and 8. In the dry box, 2.5 mol % of catalyst (0.0052 mmol) was dissolved in $C_6D_6$ (0.65 mL) in an NMR tube fitted with a teflon septum screw-cap. The resulting solution was allowed to equilibrate in the NMR probe at 60° C. Diethyldiallyl malonate (50 µL, 0.207 mmol, 0.30 M) was injected into the NMR tube neat and the reaction was monitored by $^1$H NMR spectroscopy (FIG. 14). The olefinic resonances integrals of the product relative to that of the starting material were measured with the residual protio solvent peak used as an internal standard.

EXAMPLE 19

ROMP of Dicyclopentadiene (DCPD) using Catalysts 2a and 2b

Figure 15:
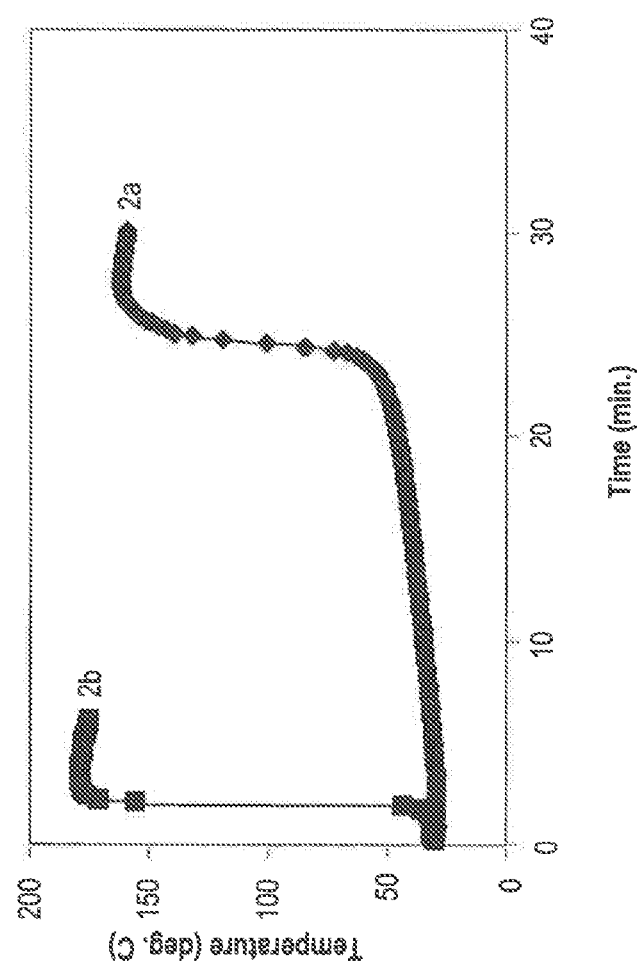
FIG. 15 provides the exotherms for the ROMP reaction catalyzed by catalysts 2a and 2b, as described in Example 19.

Dicyclopentadiene containing 3.5% of tricyclopentadiene (100 g) was polymerized by addition of catalyst (monomer/catalyst=30,000:1 mole:mole) at 30° C. The polymerization exotherms for the polymerization catalyzed by catalysts 2a and 2b were measured and are shown in FIG. 15. In the same way that catalyst 2b is much slower that 2a in RCM, 2b also initiates the ROMP of DCPD more slowly than 2a. A ROMP of DCPD using 2a reaches its exotherm within 3 minutes, while the same polymerization catalyzed by 2b requires more than 25 minutes.

While not intending to be bound by theoretical considerations, the difference in reactivity between 2a and 2b may be due to the fact that the pyridine ligand in 2a is trans to the strongly σ-donating NHC ligand and therefore dissociates to give the active 14-electron species much faster than in 2b. The difference in activity between 2a and 2b may be purely due to a disparity in initiation rates and does not give any clues regarding the conformation of the metallocyclobutane metathesis intermediates. In other words, the fact that 2a is a faster catalyst than 2b does not imply that the olefin approaching the 14-electron species must necessarily bind trans to the NHC ligand [see, e.g., Trnka, T. M.; Day, M. W.; Grubbs, R. H. *Organometallics* 2001, 20, 3845-3847 for a discussion on the conformation of olefin metathesis intermediates]. Substitution on the pyridine ring has a much less dramatic effect on catalytic activity.

Figure 16:
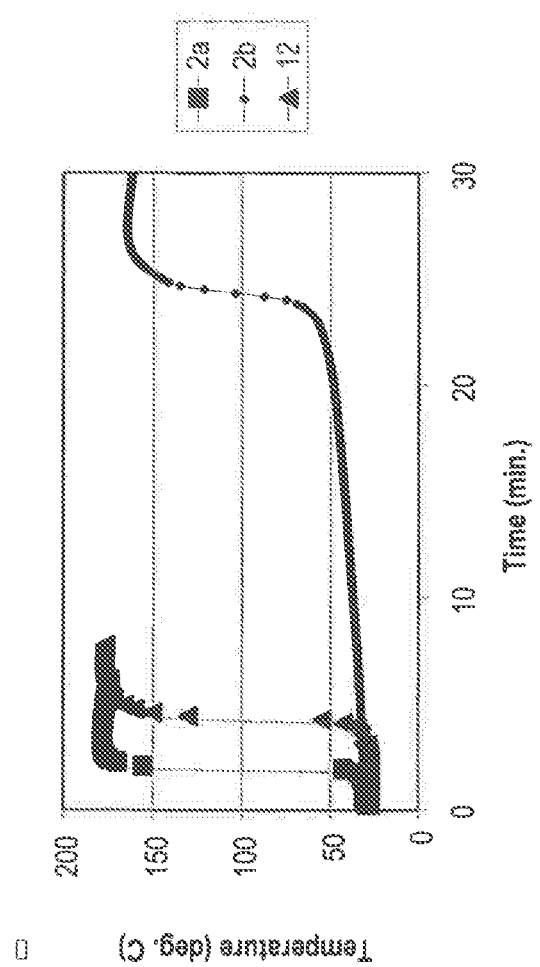
FIG. 16 provides the exotherms for the ROMP reaction catalyzed by catalysts 2a, 2b and 12, as also described in Example 19.

In the ROMP of DCPD, a reaction less sensitive to small reactivity differences, the three complexes 2a, 4 and 5 were found to have similar catalytic properties. A further ROMP was run to compare catalysts 2a, 2b, and 12, with the results given in FIG. 16.

EXAMPLE 20

ROMP of Dicyclopentadiene (DCPD) using Mixtures of Catalysts 2a and 2b

Dicyclopentadiene containing 3.5% of tricyclopentadiene (100 g) was polymerized by addition of catalyst (monomer/catalyst=40,000:1 mole:mole) at 30° C. The polymerization exotherms for the polymerization catalyzed by mixtures of catalysts 2a and 2b at various ratios of the catalysts were measured and are shown in FIG. 17.

Figure 17:
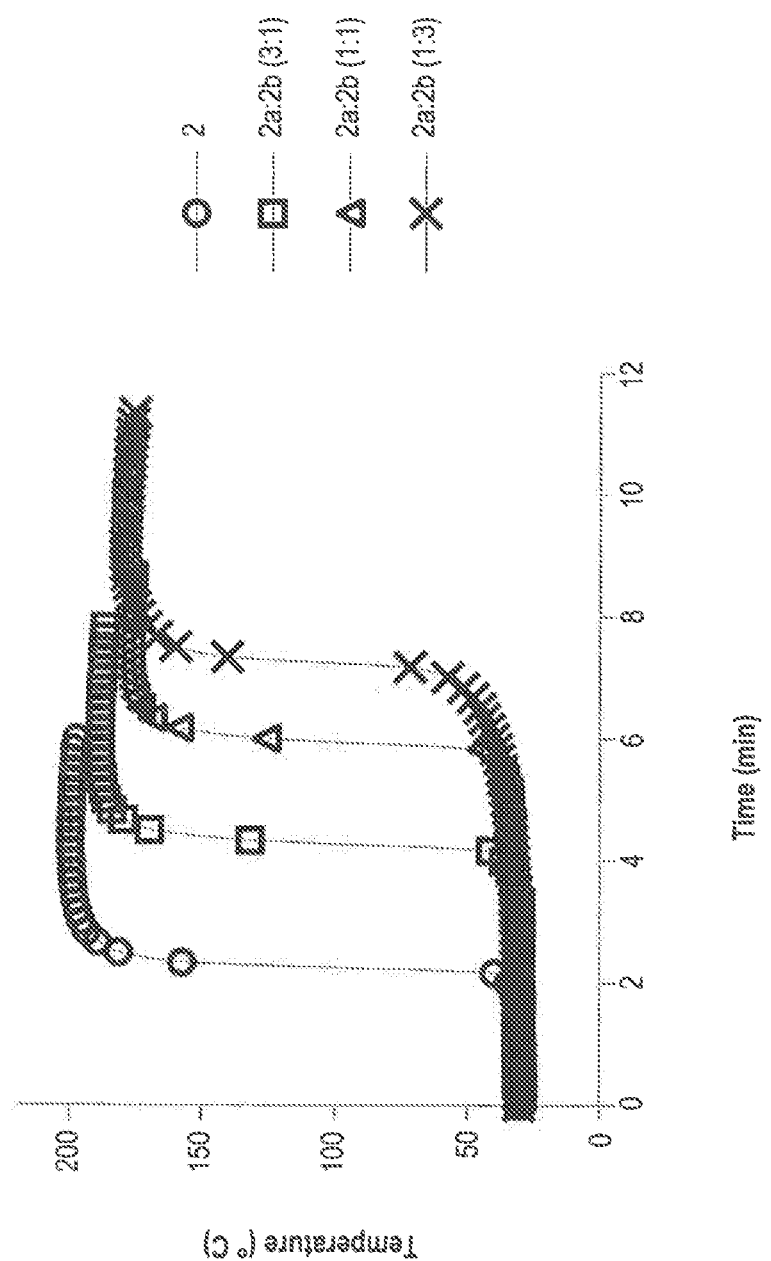
FIG. 17 provides the exotherms for the ROMP reactions catalyzed using different mixtures of 2a and 2b, as described in Example 20.

As shown in FIG. 17, the slow isomerization process and large activity difference between catalysts 2a and 2b allows for this catalytic system to be tuned by partially isomerizing 2a to a 2a:2b mixture with the desired initiation rate. Indeed, the use of varying 2a:2b mixtures for the ROMP of DCPD allowed for the control of the times to exotherm as shown in FIG. 17.

EXAMPLE 21

ROMP of Dicyclopentadiene (DCPD) using Catalysts 2a, 7 and 8

Figure 18:
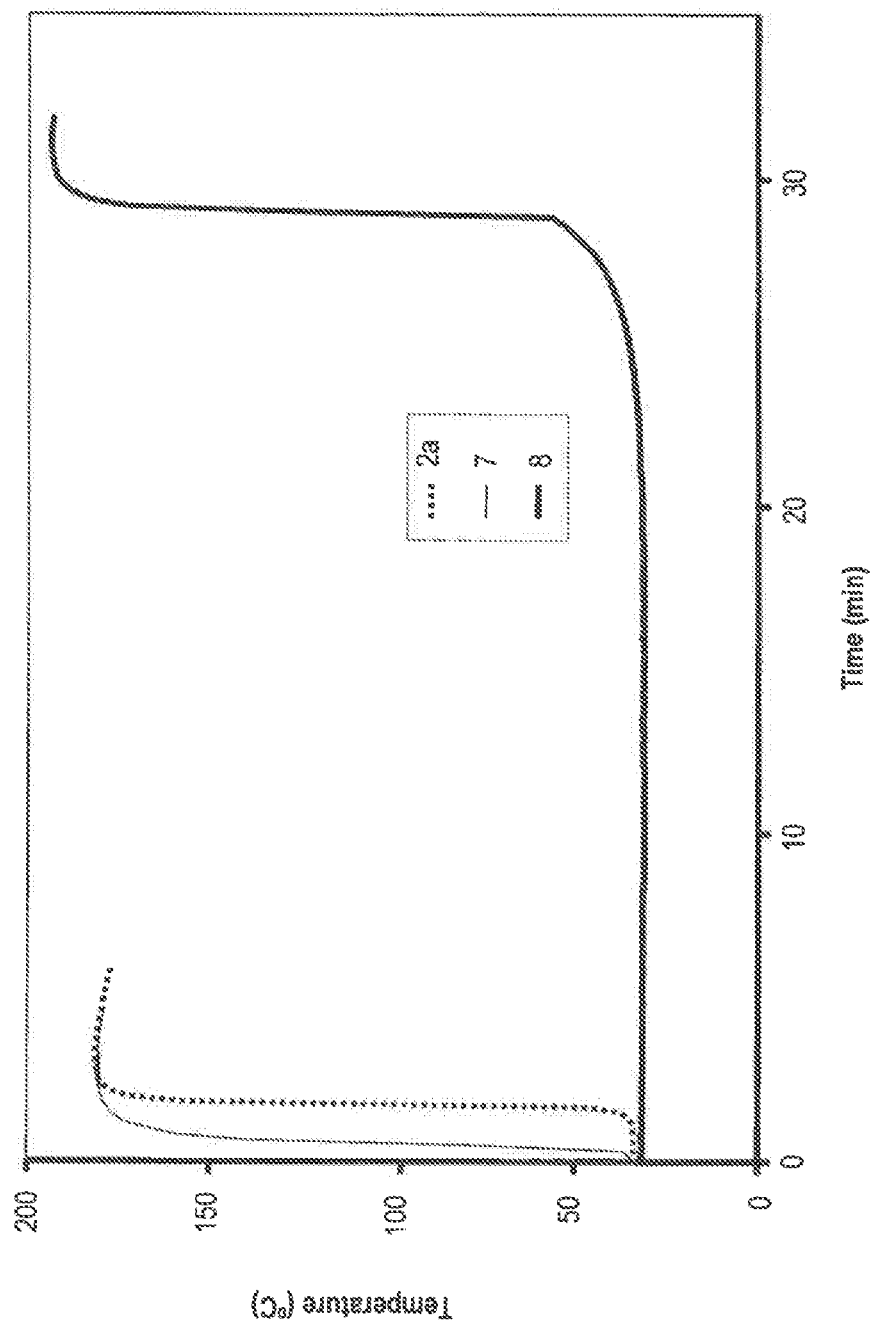
FIG. 18 provides the exotherms for the ROMP reaction catalyzed by catalysts 2a, 7 and 8, as described in Example 21.

Dicyclopentadiene containing 3.5% of tricyclopentadiene (100 g) was polymerized by addition of catalyst (monomer/catalyst=40,000:1 mole:mole) at 30° C. The polymerization exotherms for the polymerization catalyzed by catalysts 2a, Ru(Ph-IM) and Ru(Cy-Im) were measured and are shown in FIG. 18.

As noted in RCM, catalyst 7 is faster than 2a, while 8 is slower than 2a. The same trend was observed in the ROMP of DCPD. These results show that the catalysts that contain an imine ligand Ru(R-Im) (where R is for instance an alkyl or aryl group) can easily be tuned by varying the steric and electronic properties of the R group on the imine.

We claim:
1. A method for catalyzing an olefin metathesis reaction, comprising contacting an olefinic reactant with a complex having the structure of formula (I)

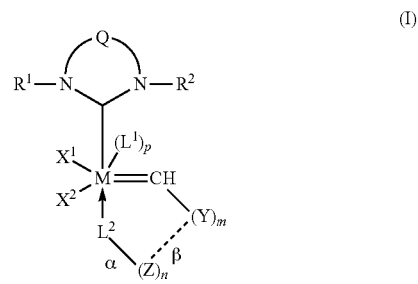

wherein:
α and β represent single bonds or unsaturated bonds, with the proviso that α and β cannot both be unsaturated bonds;
M is a Group 8 transition metal;
$R^1$ and $R^2$ are independently selected from hydrogen, hydrocarbyl, substituted hydrocarbyl, heteroatom-containing hydrocarbyl, substituted heteroatom-containing hydrocarbyl, and functional groups;
Q is an organic diradical;
$X^1$ and $X^2$ are anionic ligands, and may be the same or different;

L¹ is a neutral electron donor ligand, and p is zero or 1;

when α is a single bond, L² is selected from NR⁷R⁸, PR⁷R⁸, N=CR⁷R⁸, and R⁷C=NR⁸, where R⁷ and R⁸ are independently selected from substituted and/or heteroatom-containing $C_1$-$C_{20}$ alkyl, $C_2$-$C_{20}$ alkenyl, $C_2$-$C_{20}$ alkynyl, and $C_5$-$C_{24}$ aryl, or R⁷ and R⁸ can be taken together to form a heterocyclic ring;

when α is an unsaturated bond, L² is selected from NR' and PR⁷, where R⁷ is as defined previously, or L² and Z represent adjacent atoms in an aromatic ring;

Y and Z are linkages independently selected from hydrocarbylene, substituted hydrocarbylene, heteroatom-containing hydrocarbylene, substituted heteroatom-containing hydrocarbylene, —O—, —S—, —NR⁹, and —PR⁹—, wherein R⁹ is selected from hydrocarbyl, substituted hydrocarbyl, heteroatom-containing hydrocarbyl, and substituted heteroatom-containing hydrocarbyl, and further wherein Y and Z may represent adjacent atoms in an aromatic ring;

m is zero or 1;

n is zero or 1; and wherein

L² and the ligand containing Q are bonded to M in a trans orientation, and wherein the olefinic reactant and the complex having the structure of formula (I) are contacted under reaction conditions selected to enable olefin metathesis; and wherein the complex having the structure of formula (I) exhibits a latency period when contacted with the olefinic reactant.

2. The method for catalyzing an olefin metathesis reaction according to claim 1, wherein the complex has the structure of formula (II)

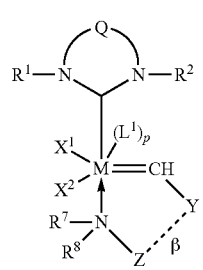

(II)

wherein:

β represents a single bond or an unsaturated bond;

M is a Group 8 transition metal;

R¹ and R² are independently selected from hydrogen, hydrocarbyl, substituted hydrocarbyl, heteroatom-containing hydrocarbyl, substituted heteroatom-containing hydrocarbyl, and functional groups;

Q is an organic diradical;

X¹ and X² are anionic ligands, and may be the same or different;

L¹ is a neutral electron donor ligand, and p is zero or 1;

R⁷ and R⁸ are independently selected from substituted and/or heteroatom-containing $C_1$-$C_{20}$ alkyl, $C_2$-$C_{20}$ alkenyl, $C_2$-$C_{20}$ alkynyl, and $C_5$-$C_{24}$ aryl, or R⁷ and R⁸ can be taken together to form a heterocyclic ring;

Y and Z are linkages independently selected from hydrocarbylene, substituted hydrocarbylene, heteroatom-containing hydrocarbylene, substituted heteroatom-containing hydrocarbylene, —O—, —S—, —NR⁹, and —PR⁹—, wherein R⁹ is selected from hydrocarbyl, substituted hydrocarbyl, heteroatom-containing hydrocarbyl, and substituted heteroatom-containing hydrocarbyl, and further wherein Y and Z may represent adjacent atoms in an aromatic ring; and wherein NR⁷R⁸ and the ligand containing Q are bonded to M in a trans orientation.

3. The method for catalyzing an olefin metathesis reaction according to claim 2, wherein R⁷ and R⁸ of the complex having the structure of formula (II) are $C_1$-$C_{12}$ alkyl or $C_5$-$C_{12}$ aryl, and Y is a substituted or unsubstituted methylene or ethylene linkage.

4. The method for catalyzing an olefin metathesis reaction according to claim 1, wherein the complex has the structure of formula (III)

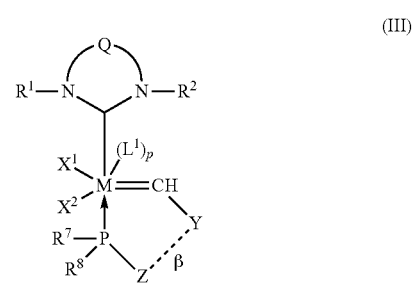

(III)

wherein:

β represents a single bond or an unsaturated bond;

M is a Group 8 transition metal;

R¹ and R² are independently selected from hydrogen, hydrocarbyl, substituted hydrocarbyl, heteroatom-containing hydrocarbyl, substituted heteroatom-containing hydrocarbyl, and functional groups;

Q is an organic diradical;

X¹ and X² are anionic ligands, and may be the same or different;

L¹ is a neutral electron donor ligand, and p is zero or 1;

R⁷ and R⁸ are independently selected from substituted and/or heteroatom-containing $C_1$-$C_{20}$ alkyl, $C_2$-$C_{20}$ alkenyl, $C_2$-$C_{20}$ alkynyl, and $C_5$-$C_{24}$ aryl, or R⁷ and R⁸ can be taken together to form a heterocyclic ring;

Y and Z are linkages independently selected from hydrocarbylene, substituted hydrocarbylene, heteroatom-containing hydrocarbylene, substituted heteroatom-containing hydrocarbylene, —O—, —S—, —NR⁹, and —PR⁹—, wherein R⁹ is selected from hydrocarbyl, substituted hydrocarbyl, heteroatom-containing hydrocarbyl, and substituted heteroatom-containing hydrocarbyl, and further wherein Y and Z may represent adjacent atoms in an aromatic ring; and wherein PR⁷R⁸ and the ligand containing Q are bonded to M in a trans orientation.

5. The method for catalyzing an olefin metathesis reaction according to claim 4, wherein R⁷ and R⁸ of the complex having the structure of formula (III) are $C_1$-$C_{12}$ alkyl or $C_5$-$C_{12}$ aryl, and Y is a substituted or unsubstituted methylene or ethylene linkage.

6. The method for catalyzing an olefin metathesis reaction according to claim 5, wherein R⁷ and R⁸ of the complex having the structure of formula (III) are phenyl and Y is ethylene.

7. The method for catalyzing an olefin metathesis reaction according to claim 1, wherein the complex has the structure of formula (IV)

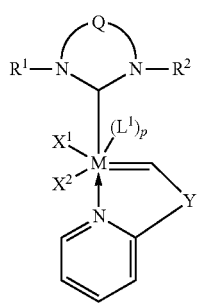

(IV)

wherein:
M is a Group 8 transition metal;
R¹ and R² are independently selected from hydrogen, hydrocarbyl, substituted hydrocarbyl, heteroatom-containing hydrocarbyl, substituted heteroatom-containing hydrocarbyl, and functional groups;
Q is an organic diradical;
X¹ and X² are anionic ligands, and may be the same or different;
L¹ is a neutral electron donor ligand, and p is zero or 1;
Y is a linkage selected from hydrocarbylene, substituted hydrocarbylene, heteroatom-containing hydrocarbylene, substituted heteroatom-containing hydrocarbylene, —O—, —S—, —NR⁹, and —PR⁹—, wherein R⁹ is selected from hydrocarbyl, substituted hydrocarbyl, heteroatom-containing hydrocarbyl, and substituted heteroatom-containing hydrocarbyl; and wherein
the complex has a pyridine ligand,
wherein the pyridine ligand and the ligand containing Q are bonded to M in a trans orientation.

8. The method for catalyzing an olefin metathesis reaction according to claim 1, wherein the complex has the structure of formula (V)

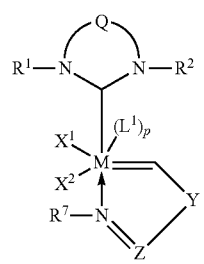

(V)

wherein:
M is a Group 8 transition metal;
R¹ and R² are independently selected from hydrogen, hydrocarbyl, substituted hydrocarbyl, heteroatom-containing hydrocarbyl, substituted heteroatom-containing hydrocarbyl, and functional groups;
Q is an organic diradical;
X¹ and X² are anionic ligands, and may be the same or different;
L¹ is a neutral electron donor ligand, and p is zero or 1; and
R⁷ is selected from substituted and/or heteroatom-containing C₁-C₂₀ alkyl, C₂-C₂₀ alkenyl, C₂-C₂₀ alkynyl, and C₅-C₂₄ aryl;
Y and Z are linkages independently selected from hydrocarbylene, substituted hydrocarbylene, heteroatom-containing hydrocarbylene, substituted heteroatom-containing hydrocarbylene, —O—, —S—, —NR⁹, and —PR⁹—, wherein R⁹ is selected from hydrocarbyl, substituted hydrocarbyl, heteroatom-containing hydrocarbyl, and substituted heteroatom-containing hydrocarbyl; and wherein NR' and the ligand containing Q are bonded to M in a trans orientation.

9. The method for catalyzing an olefin metathesis reaction according to claim 1, wherein the complex is selected from:

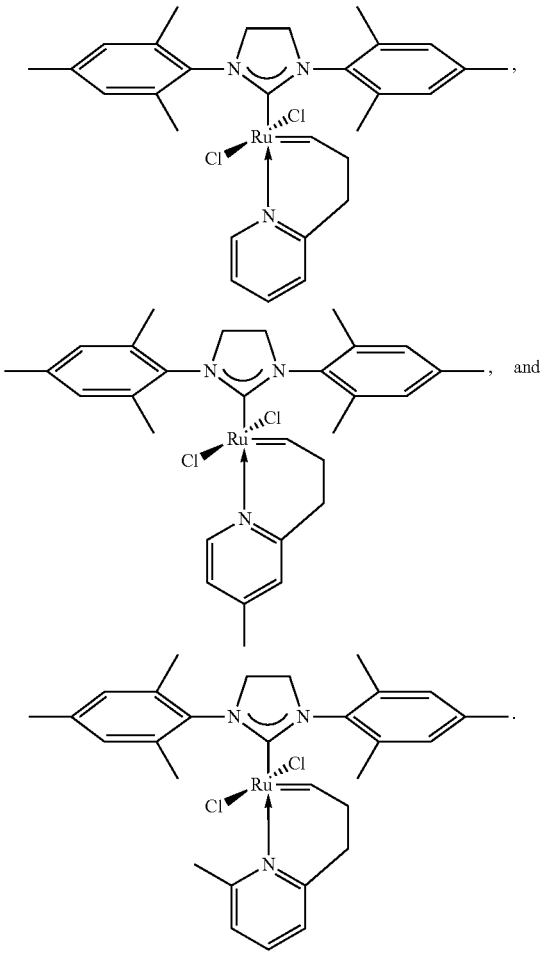

10. The method for catalyzing an olefin metathesis reaction according to claim 1, wherein the complex has the structure:

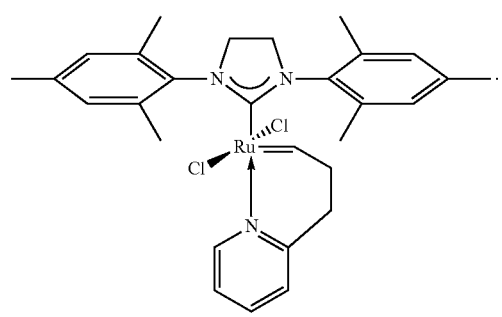

11. The method for catalyzing an olefin metathesis reaction according to claim 1, wherein the complex has the structure:

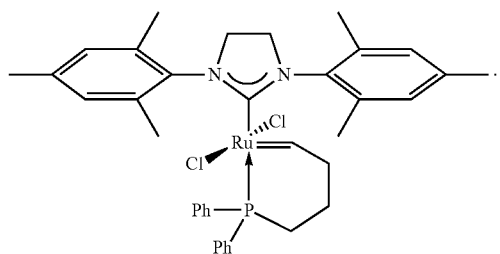

12. The method for catalyzing an olefin metathesis reaction according to claim 1, wherein the complex is selected from:

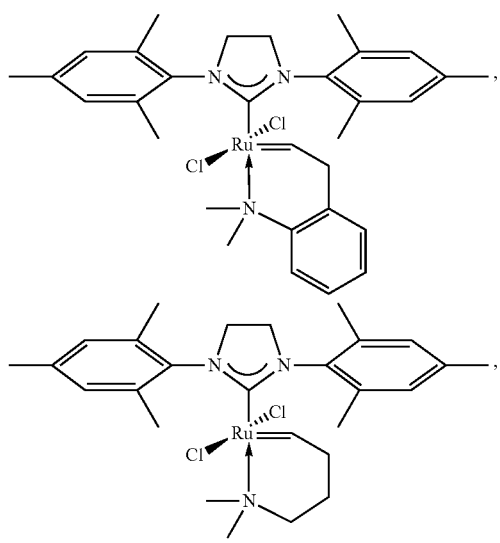

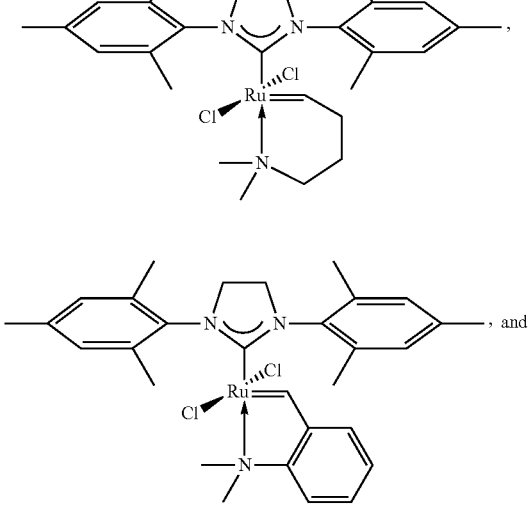

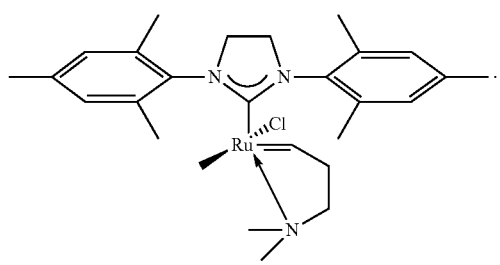

13. The method for catalyzing an olefin metathesis reaction according to claim 1, wherein the complex is selected from:

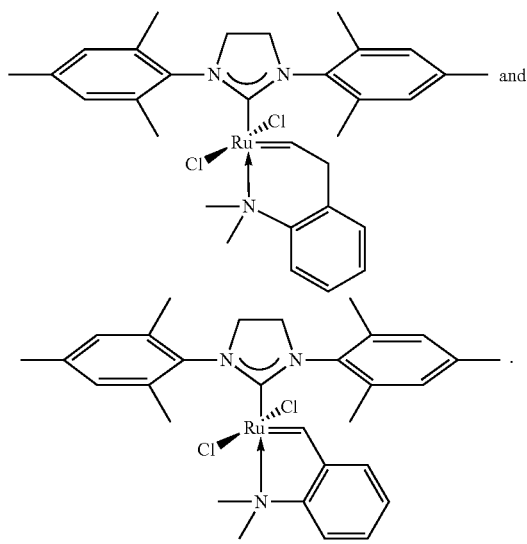

14. The method for catalyzing an olefin metathesis reaction according to claim 1, wherein the complex is selected from:

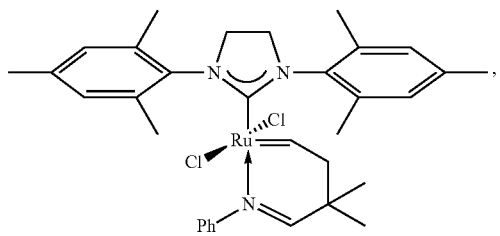

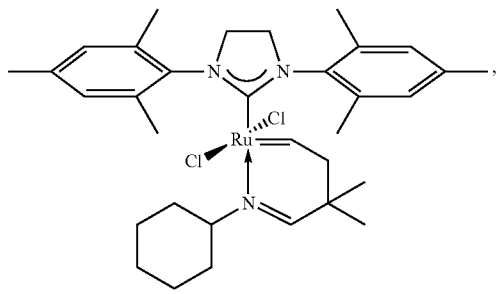

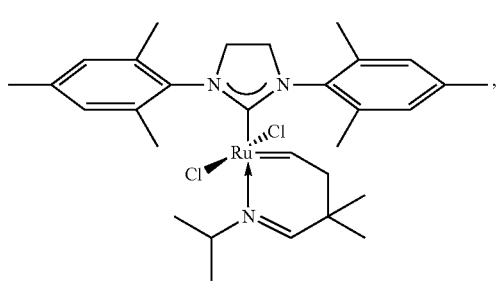

-continued

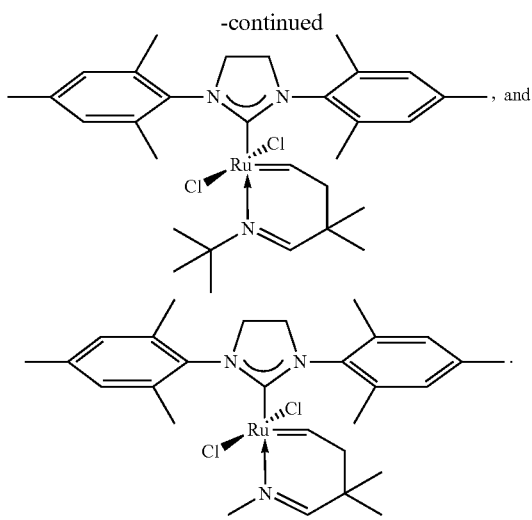

, and

15. A method for controlling the reaction latency period of an olefin metathesis reaction, comprising combining an olefin metathesis reaction mixture with an organometallic complex comprising a Group 8 transition metal having an N-heterocyclic carbene ligand and a chelating carbene ligand, wherein the olefin metathesis reaction mixture and the organometallic complex are combined under reaction conditions selected to enable olefin metathesis, and wherein the organometallic complex exhibits a latency period of at least two minutes when combined with the olefin metathesis reaction mixture.

16. The method for controlling the reaction latency period of an olefin metathesis reaction according to claim 15, wherein the olefin metathesis reaction is ring opening metathesis polymerization.

17. The method for controlling the reaction latency period of an olefin metathesis reaction according to claim 15, wherein the olefin metathesis reaction is ring closing metathesis.

18. A method for controlling the reaction latency period of an olefin metathesis reaction, comprising combining an olefin metathesis reaction mixture with a complex having the structure of formula (I)

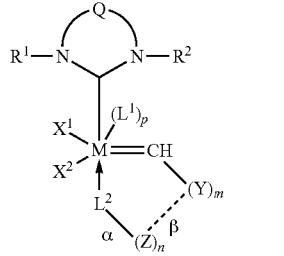

(I)

wherein:
α and β represent single bonds or unsaturated bonds, with the proviso that α and β cannot both be unsaturated bonds;

M is a Group 8 transition metal;
$R^1$ and $R^2$ are independently selected from hydrogen, hydrocarbyl, substituted hydrocarbyl, heteroatom-containing hydrocarbyl, substituted heteroatom-containing hydrocarbyl, and functional groups;
Q is an organic diradical;
$X^1$ and $X^2$ are anionic ligands, and may be the same or different;
$L^1$ is a neutral electron donor ligand, and p is zero or 1;
when α is a single bond, $L^2$ is selected from $NR^7R^8$, $PR^7R^8$, $N=CR^7R^8$, and $R^7C=NR^8$, where $R^7$ and $R^8$ are independently selected from substituted and/or heteroatom-containing $C_1$-$C_{20}$ alkyl, $C_2$-$C_{20}$ alkenyl, $C_2$-$C_{20}$ alkynyl, and $C_5$-$C_{24}$ aryl, or $R^7$ and $R^8$ can be taken together to form a heterocyclic ring;
when α is an unsaturated bond, $L^2$ is selected from NR' and $PR^7$, where $R^7$ is as defined previously, or $L^2$ and Z represent adjacent atoms in an aromatic ring;
Y and Z are linkages independently selected from hydrocarbylene, substituted hydrocarbylene, heteroatom-containing hydrocarbylene, substituted heteroatom-containing hydrocarbylene, —O—, —S—, —$NR^9$, and —$PR^9$—, wherein $R^9$ is selected from hydrocarbyl, substituted hydrocarbyl, heteroatom-containing hydrocarbyl, and substituted heteroatom-containing hydrocarbyl, and further wherein Y and Z may represent adjacent atoms in an aromatic ring;
m is zero or 1;
n is zero or 1; and wherein
$L^2$ and the ligand containing Q are bonded to M in a trans orientation, and wherein the olefin metathesis reaction mixture and the complex having the structure of formula (I) are combined under reaction conditions selected to enable olefin metathesis.

19. The method for controlling the reaction latency period of an olefin metathesis reaction according to claim 18, wherein the complex having the structure of formula (I) exhibits a latency period when combined with the olefin metathesis reaction mixture.

20. The method for controlling the reaction latency period of an olefin metathesis reaction according to claim 19, wherein the latency period is at least two minutes.

21. The method for controlling the reaction latency period of an olefin metathesis reaction according to claim 18, wherein the complex has the structure:

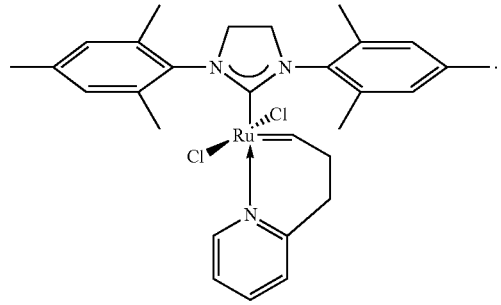

* * * * *